United States Patent
Floyd et al.

(10) Patent No.: US 6,911,455 B2
(45) Date of Patent: Jun. 28, 2005

(54) METHODS FOR PREPARING PHARMACEUTICAL FORMULATIONS

(75) Inventors: Alison G. Floyd, Durham, NC (US); Mir A Hashim, Durham, NC (US); Peiyuan Lin, Durham, NC (US); Robert A. Mook, Durham, NC (US); Andrea Sefler, Durham, NC (US); Kathleen Cornell Meserve, Durham, NC (US); Patricia Neal Ricciarelli, Durham, NC (US); Timothy David Spitzer, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 325 days.

(21) Appl. No.: 10/149,722

(22) PCT Filed: Dec. 13, 2000

(86) PCT No.: PCT/US00/33772

§ 371 (c)(1),
(2), (4) Date: Jun. 13, 2002

(87) PCT Pub. No.: WO01/45741

PCT Pub. Date: Jun. 28, 2001

(65) Prior Publication Data

US 2003/0096839 A1 May 22, 2003

Related U.S. Application Data

(60) Provisional application No. 60/171,696, filed on Dec. 22, 1999.

(51) Int. Cl.$^7$ ........................ A61K 31/47; A61K 31/165
(52) U.S. Cl. ......................................... 514/308; 424/44
(58) Field of Search ......................................... 514/308

(56) References Cited

U.S. PATENT DOCUMENTS

| | | | | |
|---|---|---|---|---|
| 4,309,408 A | * | 1/1982 | Pathak et al. ................. | 424/44 |
| 5,437,872 A | * | 8/1995 | Lee ............................. | 424/464 |
| 5,767,112 A | | 6/1998 | Poli et al. | |
| 6,099,864 A | * | 8/2000 | Morrison et al. ........... | 424/489 |
| 6,177,445 B1 | * | 1/2001 | Bigham et al. .............. | 514/308 |
| 6,187,789 B1 | * | 2/2001 | Bigham et al. .............. | 514/308 |
| 6,380,356 B1 | * | 4/2002 | Griffin et al. ............... | 530/319 |

FOREIGN PATENT DOCUMENTS

| | | |
|---|---|---|
| EP | 0 707 853 | 4/1996 |
| WO | WO 98 42674 | 10/1998 |
| WO | WO 98 42675 | 10/1998 |
| WO | WO 99 27914 | 6/1999 |

OTHER PUBLICATIONS

Wien, R. "The Pharmacological Actions of Certain Aromatic Diamidines Possessing Trypanocidal Activity," Ann. Trop. Med. Parasit (1943), 37.

MacIntosh, F.C., et al. "The Liberation of Histamine by Certain Organic Bases," J. Physiol. (1949) 109, 190–219.

West, G.B. "Ethylenediamine Tetraacetic Acid and Histamine Release from Rat Mast Cells," Int. Archs Allergy Appl. Immun. 68:399–401, 1982.

Read, G.W., et al. "Competitive Inhibition of 48/80–Induced Histamine Release by Benzalkonium Chloride and Its Analogs and the Polyamine Receptor in Mast Cells," Journal of Pharmacology and Experimental Therapeutics, 1982, vol. 222, no.

Frisk–Holmberg, M., et al. "Histamine Release from Rat Peritoneal Mast Cells and Cat Paws Induced by Some Neuromuscular Blocking Agents," ACTA Physiol. Scand. 1971, 81:367–375.

"Histamine Release by Drugs, Peptides, Venoms, and Other Agents," Goodman & Gilman's The Pharmacological Basis of Therapeutics, Ninth Edition, 1996, Chapter 25, pp. 583.

* cited by examiner

Primary Examiner—Vickie Kim
(74) Attorney, Agent, or Firm—Jennifer L. Fox

(57) ABSTRACT

The invention relates to pharmaceutical formulations and methods for preparing pharmaceutical formulations of histamine releasers. The present invention provides methods for determining the concentration of physiologically acceptable excipients for use in the formulations of the invention. The present invention also provides methods for suppressing pharmaceutically-induced histamine release by administering to an animal, the formulations of the present invention. A kit useful for preparing pharmaceutical formulations of histamine releasers is also provided.

32 Claims, 2 Drawing Sheets

METHODS FOR PREPARING PHARMACEUTICAL FORMULATIONS

CROSS-REFERENCES TO RELATED APPLICATIONS

This application is a Rule 371 Application of PCT Application No. US00/33772, filed 13 Dec. 2000, which claims priority to U.S. application Ser. No. 60/171,696, filed 22 Dec. 1999.

BACKGROUND OF THE INVENTION

The present invention relates to the use of pharmaceutically active agents known to cause histamine release when intravenously administered to an animal. More particularly the present invention relates to new methods of using such pharmaceutically active agents and new formulations of such agents which address pharmaceutically-induced histamine release.

The cardiovascular and respiratory effects indicative of undesirable degrees of histamine release which are specific to some conventional pharmacological agents have been troubling clinicians for decades. The clinical observations associated with an undesirable degree of histamine release are typified by cutaneous flushing about the face, neck and/or chest, sometimes accompanied by hypotension and/or tachycardia and/or nausea and vomiting. In some cases, the physical manifestations of an undesirably high degree of histamine release can include very serious and potentially fatal reactions such as bronchospasm, wheezing, and anaphylactoid reactions and anaphylactic shock. An explanation of the reason(s) that these pharmacological agents cause histamine release in vivo has eluded scientists for years.

Conventional pharmacological agents which are known to cause or suspected to be capable of causing histamine release include intravenously administered hypnotics, analgesics, sedatives, optiates, anesthetics, neuromuscular blocking agents (i.e., "neuromuscular blockers"), contrast agents employed in imaging (i.e., radiographic contrast media, radio imaging agents and other contrast agents, hereinafter collectively "imaging agents"), hormones for diagnostic procedures, and certain antibiotics, NSAIDs, anticoagulants, ACE inhibitors and benzodiazepine receptor antagonists. These agents may be administered intravenously as a bolus or rapid infusion, which can, in addition to their desired therapeutic, diagnostic or medicinal effect, cause the release of histamine. Histamine release is often the most prevalent adverse reaction of certain of these pharmacological agents.

Histamine release could occur through both immunologic and non-immunologic mechanisms. The more immediate or rapid reactions elicited by these pharmacological agents are believed to occur via release of histamine via a non-immunologic mechanism. The latter are often referred to as anaphylactoid reactions.

The precise mechanism by which these drugs cause the release of histamine is not clear. Mast cells and basophils are possible sources of the released histamine, but other in vivo sources may also exist. Mechanistic studies, especially studies conducted in vitro with mast cells are complicated by the tremendous heterogeneity that exists not only between species, but within a single individual. Given the number of different sources of histamine, it is possible that different mechanisms in different cells and tissue may be involved at any one time.

Clinically, it is known that slowing the rate of injection of these agents from 5 seconds to 30 seconds decreases the incidence of cardiovascular effects typical of histamine release. Slowing the rate of administration is currently the preferred method of avoiding the risks associated with substantial histamine release. However, slowing the rate of administration is not an acceptable course of action in some clinical situations. For example, slowing the rate of administration is unacceptable in emergency medical situations, especially when anesthesia and intubation prior to emergency surgical procedures must occur rapidly. Furthermore, it is known that slowing administration of certain pharmacological agents can disproportionately decrease the speed of onset of activity and/or the potency of the drug.

There remains a need in the art for methods of addressing the histamine release side effect associated with these pharmacological agents.

SUMMARY OF THE INVENTION

Figure 1:
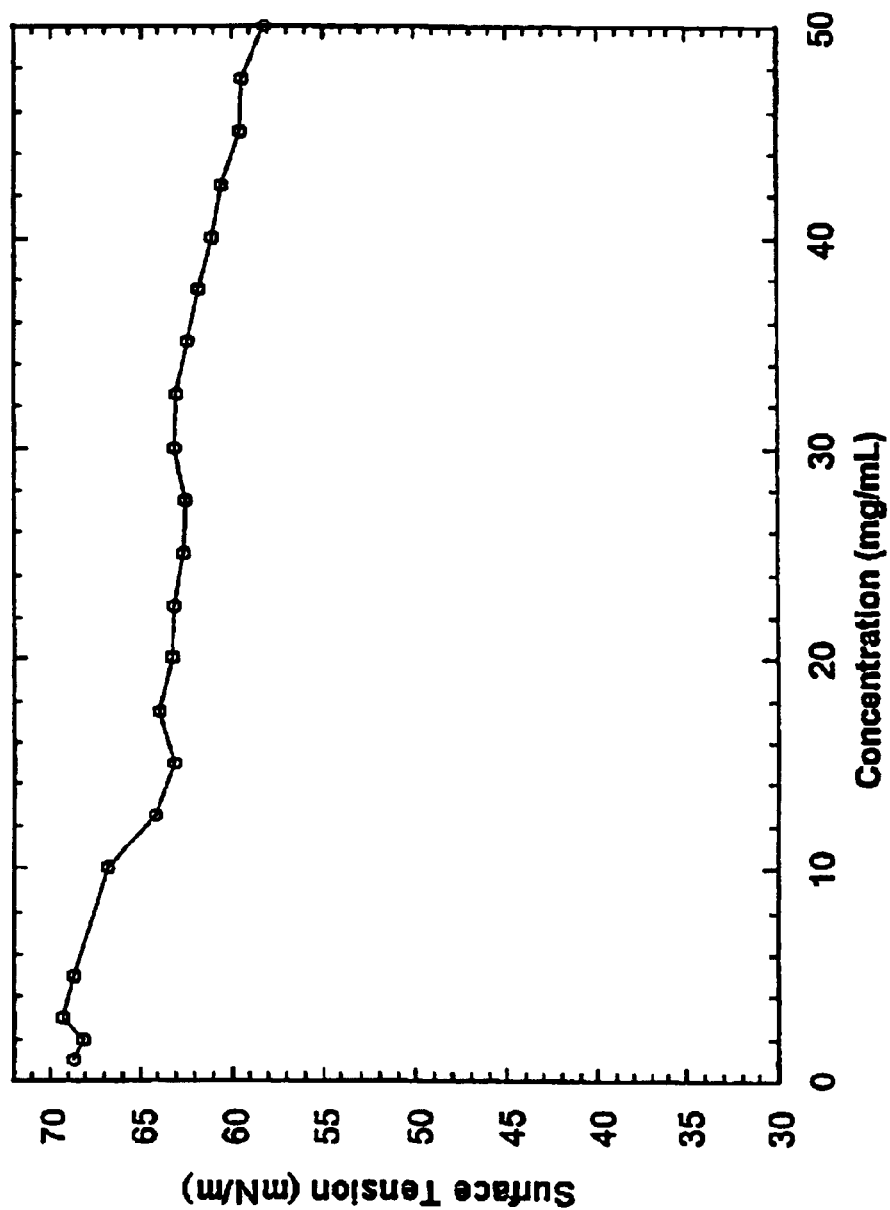
FIG. 1 is a plot of the surface tension (mN/m) versus increasing concentration of Z-2-Chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride (designated "Compound 1") (mg/mL).

According to a first aspect of the invention there is provided a method for preparing a pharmaceutical formulation containing a histamine releaser and a physiologically acceptable excipient. The method comprises combining a therapeutically effective amount of the histamine releaser with a concentration of the physiologically acceptable excipient. The concentration of the physiologically acceptable excipient, when combined in an aqueous solution with the histamine releaser at or above critical micelle concentration, is sufficient to reduce aggregation of the histamine releaser in the aqueous solution by at least about 25 percent compared to aggregation of the histamine releaser in the aqueous solution containing substantially no physiologically acceptable excipient.

According to a second aspect of the invention, there is provided another method for preparing a pharmaceutical formulation containing a histamine releaser and a physiologically acceptable excipient. The method comprises combining a therapeutically effective amount of the histamine releaser with the physiologically acceptable excipient. The physiologically acceptable excipient is present in a concentration determined by a method comprising the steps of: a) measuring aggregation of the histamine releaser in a reference solution consisting essentially of the histamine releaser in a concentration at or above the critical micelle concentration in an aqueous solution; b) measuring aggregation of the histamine releaser in a comparative solution consisting essentially of the histamine releaser and a pre-selected concentration of the physiologically acceptable excipient in the aqueous solution, wherein the concentration of the histamine releaser in the comparative solution is substantially the same as the concentration of the histamine releaser in the reference solution; c) optionally repeating step b) one or more times with a comparative solution having a different pre-selected concentration of the physiologically acceptable excipient d) identifying a concentration of physiologically acceptable excipient that is sufficient to reduce aggregation of the histamine releaser in the comparative solution by at least about 25 percent compared to aggregation of the histamine releaser in the reference solution. The identified concentration of step d) is the concentration of the physiologically acceptable excipient for combining with the histamine releaser to prepare the pharmaceutical formulation.

According to a third aspect, there is provided another method of preparing a pharmaceutical formulation containing a histamine releaser and a physiologically acceptable excipient. The method comprises combining a therapeutically effective amount of the histamine releaser with a concentration of physiologically acceptable excipient. The concentration of the physiologically acceptable excipient is determined by a method comprising the steps of: a) measuring histamine release from a histamine-containing biological sample in a reference mixture consisting essentially of: i) the histamine-containing biological sample in a medium and ii) an aqueous solution of the histamine releaser at a concentration sufficient to cause histamine release from the histamine-containing biological sample; b) measuring histamine release from the histamine-containing biological sample in a comparative mixture consisting essentially of: i) the histamine-containing biological sample in medium and ii) an aqueous solution of the histamine releaser and a pre-selected concentration of the physiologically acceptable excipient, wherein the histamine releaser in the comparative mixture is present in a concentration which is substantially the same as the concentration of histamine releaser in the reference mixture of step a); c) optionally repeating step b) one or more times with a comparative mixture having a different pre-selected concentration of the physiologically acceptable excipient; and d) identifying a concentration of the physiologically acceptable excipient sufficient to reduce histamine release from the histamine-containing biological sample in the comparative mixture by at least about 10 percent compared to histamine release from the histamine-containing biological sample in the reference mixture. The identified concentration of step d) is the concentration of physiologically acceptable excipient for combining with the histamine releaser to prepare the pharmaceutical formulation.

According to a fourth aspect of the present invention, there are provided methods for determining a concentration of a physiologically acceptable excipient for combining with the histamine releaser to prepare the pharmaceutical formulation. These methods are as described above in connection with methods for preparing the pharmaceutical formulations of the present invention.

According to a fifth aspect of the present invention, there is provided a method for determining a concentration of a physiologically acceptable excipient that is sufficient to suppress pharmaceutically-induced histamine release in an animal being treated with a histamine releaser. The method comprises: a) measuring aggregation of the histamine releaser in a reference solution consisting essentially of the histamine releaser in a concentration at or above the critical micelle concentration in an aqueous solution; b) measuring aggregation of the histamine releaser in a comparative solution consisting essentially of the histamine releaser and a pre-selected concentration of the physiologically acceptable excipient in the aqueous solution, wherein the concentration of the histamine releaser in the comparative solution is substantially the same as the concentration of the histamine releaser in the reference solution; c) optionally repeating step b) one or more times with a comparative solution having a different pre-selected concentration of the physiologically acceptable excipient; d) identifying a concentration of physiologically acceptable excipient that is sufficient to reduce aggregation of the histamine releaser in the comparative solution by at least about 25 percent compared to aggregation of the histamine releaser in the reference solution. The identified concentration of step d) is the concentration of the physiologically acceptable excipient that is sufficient to suppress pharmaceutically-induced histamine release in an animal being treated with a histamine releaser. The foregoing method may also be employed to determine a concentration of a physiologically acceptable excipient which when combined in an aqueous solution with the histamine releaser at or above critical micelle concentration, is sufficient to reduce aggregation of the histamine releaser in the aqueous solution by at least about 25 percent compared to aggregation of the histamine releaser in an aqueous solution containing substantially no physiologically acceptable excipient.

According to a sixth aspect of the present invention, there is provided another method for determining a concentration of a physiologically acceptable excipient that is sufficient to suppress pharmaceutically-induced histamine release in an animal being treated with a histamine releaser. The method comprises: a) measuring histamine release from a histamine-containing biological sample in a reference mixture consisting essentially of: i) the histamine-containing biological sample in a medium and ii) an aqueous solution of the histamine releaser at a concentration sufficient to cause histamine release from the histamine-containing biological sample; b) measuring histamine release from the histamine-containing biological sample in a comparative mixture consisting essentially of: i) the histamine-containing biological sample in medium and ii) an aqueous solution of the histamine releaser and a pre-selected concentration of the physiologically acceptable excipient, wherein the histamine releaser in the comparative mixture is present in a concentration which is substantially the same as the concentration of histamine releaser in the reference mixture of step a); c) optionally repeating step b) one or more times with a comparative mixture having a different pre-selected concentration of the physiologically acceptable excipient; and d) identifying a concentration of the physiologically acceptable excipient sufficient to reduce histamine release from the histamine-containing biological sample in the comparative mixture by at least about 10 percent compared to histamine release from the histamine-containing biological sample in the reference mixture. The identified concentration of step d) is the concentration of the physiologically acceptable excipient that is sufficient to suppress pharmaceutically-induced histamine release in an animal being treated with a histamine releaser. This concentration of excipient is advantageously employed for the preparation of pharmaceutical formulations of the histamine releaser. The foregoing method may also be employed to determine a concentration of a physiologically acceptable excipient which when combined in a saline solution with the histamine releaser at or above critical micelle concentration, is sufficient to reduce aggregation of the histamine releaser in the saline solution by at least about 25 percent compared to aggregation of the histamine releaser in a saline solution containing substantially no physiologically acceptable excipient.

According to another aspect, the present invention provides pharmaceutical formulations comprising a histamine releaser and a concentration of physiologically acceptable excipient. The pharmaceutical formulations may be prepared according to any of the methods of the present invention. The concentration of physiologically acceptable excipient may be determined according to any of the methods of the present invention. The present invention provides a pharmaceutical formulation comprising a histamine releaser and a physiologically acceptable excipient wherein the concentration of the physiologically acceptable excipient is sufficient to suppress pharmaceutically-induced histamine release.

According to another aspect of the invention there is provided a method for suppressing pharmaceutically-induced histamine release in an animal being treated with a histamine releaser. The method comprises administering to the animal a pharmaceutical formulation according to the present invention.

In another aspect, the present invention provides use of a pharmaceutical formulation according to the invention for the manufacture of a medicament for suppressing pharmaceutically-induced histamine release in an animal being treated with the histamine releaser.

According to another aspect of the invention, there is provided a method for preventing cardiovascular and respiratory effects mediated by pharmaceutically-induced histamine release in an animal being treated with a histamine releaser. The method comprises administering to the animal a pharmaceutical formulation according to the present invention.

In another aspect, the present invention provides use of a pharmaceutical formulation according to the invention for the manufacture of a medicament for preventing cardiovascular and respiratory effects mediated by pharmaceutically-induced histamine release in an animal being treated with the histamine releaser.

In yet another aspect, the present invention provides a kit for preparing a pharmaceutical formulation of a histamine releaser. The kit comprises a) a physiologically acceptable excipient, and b) instructions for preparing the pharmaceutical formulation according to the methods of the present invention.

A preferred histamine releaser for use in the pharmaceutical formulations and methods of treatment of the present invention is (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride and pharmaceutically acceptable salts thereof. Thus, in another aspect, the present invention provides a pharmaceutical formulation comprising a therapeutically effective amount of (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride and pharmaceutically acceptable salts thereof; an excipient selected from the group consisting of glycine in a concentration of from about 10 mg/mL to about 30 mg/mL, citric acid in a concentration of from about 25 mM to about 75 mM, EDTA in a concentration of from about 0.1% to about 0.5%, calcium chloride in a concentration of from about 25 mM to about 75 mM, and combinations thereof; and a physiologically acceptable diluent, wherein said pharmaceutical formulation is suitable for intravenous administration. The present invention also provides methods for suppressing pharmaceutically-induced histamine release in an animal being treated with (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride or a pharmaceutically acceptable salts thereof.

These and other aspects of the present invention are described further in the Detailed Description of the Invention, which follows and in the claims.

DETAILED DESCRIPTION OF THE INVENTION

I. Definitions

"Pharmaceutical agent" as used herein shall refer to agents having therapeutic activity (i.e., agents administered to an animal, preferably a human, for the treatment or prevention of a medical condition), agents having diagnostic activity (i.e., agents administered to an animal, preferably a human, for aiding or assisting in the diagnosis of a medical condition), and agents having other medicinal utility (i.e., agents administered to facilitate medical and/or surgical procedures) when administered to an animal, preferably a human (e.g., neuromuscular blockers, anesthetics, analgesics and the like).

"Histamine releaser" as used herein refers to a pharmaceutical agent which is selected from the group consisting of anesthetics, opiates, neuromuscular blockers, imaging agents, hormones for diagnostic procedures, tricyclic glycopeptide antibiotics, cephalosporin antibiotics, penicillin and penicillin derivative antibiotics, intravenously administered non-steroidal anti-inflammatory agents (NSAIDs), anticoagulants, ACE inhibitors, and benzodiazepine receptor antagonists, which when intravenously administered as a rapid bolus or rapid infusion to an animal, causes elevation of plasma and/or tissue concentrations of histamine above normal physiological levels. The histamine releasers are characterized by a structure having one or more hydrophilic charged (cationic or anionic) portions distanced from one or more hydrophobic portions. More particularly, "histamine releasers" include pharmaceutical agents which when intravenously administered as a rapid bolus or rapid infusion to an animal cause a histamine release in vivo which is sufficient to produce physiological manifestations selected from the group consisting of cutaneous flushing, itching, hives, edema, nausea, vomiting, elevated gastric acid secretion, vestibular effects, cardiovascular effects such as hypotension (fall in blood pressure), tachycardia (rise in heart rate), and respiratory effects such as bronchoconstriction, anaphylactoid reactions and anaphylactic shock, and combinations of any two or more of the foregoing. "Normal physiological levels of histamine" can differ among species and among individual members of a single species. Therefore, "normal physiological levels of histamine" refers to an average plasma histamine level of an untreated animal of the same species as that being treated with the histamine releaser. Normal physiological levels of histamine of various species of animals is reported in INFLAMMATION: BASIC PRINCIPLES AND CLINICAL CORRELATES (Eds. J. I. Gallin, I. M. Goldstein, and R. Snyderman, Chap. 11, *Measurement of Histamine*, p. 202, Raven Press, New York, 1992; and Bertini, S. et al., *Gen. Pharmac.* 31:625–631 (1998).

As used herein, the term "therapeutically effective amount of a histamine releaser" means an amount of the pharmaceutical agent which is a histamine releaser (defined above), which amount is sufficient to achieve the desired pharmaceutical activity (i.e., therapeutic activity, diagnostic activity or medicinal utility) of the agent. Thus, in the embodiment wherein the histamine releaser is a neuromuscular blocker, a "therapeutically effective amount of the histamine releaser" is the amount of the neuromuscular blocker which is sufficient to cause skeletal muscle relaxation in the animal to which the neuromuscular blocker is being administered. In the embodiment wherein the histamine releaser is an anesthetic, a "therapeutically effective amount of the histamine releaser" is the amount of anesthetic which is sufficient to induce anesthesia in the animal to which the anesthetic is being administered. In the embodiment wherein the histamine releaser is a an imaging agent, a "therapeutically effective amount of the histamine releaser" is the amount of imaging agent which is sufficient to produce an appropriate level of image contrast in a diagnostic procedure in the animal to which the imaging agent is being administered. One skilled in the art can readily determine the therapeutically effective amount of a particular histamine releaser based upon the foregoing explanation and examples, and conventional knowledge in the art regarding these pharmaceutical agents.

The term "physiologically acceptable excipient" means an agent, other than water, which is utilized in the formulation of a pharmaceutical agent as a pharmaceutical formulation, which is not deleterious to the animal to which the formulation will be administered, and which does not substantially affect the pharmaceutical activity of the pharmaceutical agent with which it is formulated. Typically, the physiologically acceptable excipients are employed for the purpose of facilitating formulation of the pharmaceutically active agent.

The term "aqueous solution" as used herein refers to solutions containing water (including deuterated water), preferably distilled water, and "saline solutions" (defined below), and which solutions contain substantially no other additives, but which may be pH adjusted with hydrochloric acid or sodium hydroxide, as may be necessary or desirable to stabilize or facilitate solubilization of certain histamine releasers in aqueous solution.

The term "saline solution" as used herein refers to solutions containing approximately 0.9% sodium chloride solubilized in water (including deuterated water), preferably distilled water, and which solutions contain substantially no other additives but may be pH adjusted with hydrochloric acid or sodium hydroxide as may be necessary or desirable to stabilize or facilitate solubilization of certain histamine releasers in the saline solution.

The term "aggregation" as used herein refers to the average aggregate size of a pharmaceutical agent, solubilized in aqueous solution. Aggregate size can be a function of the conformation of the molecules or aggregates, or the number of molecules forming the aggregate, or the hydrodynamic radius of the aggregate.

II. Histamine Release Generally

Although the reason(s) that these histamine releasers induce histamine release have eluded scientists for years, our studies suggest that histamine release is the result of a combination of at least two, possibly related, factors; namely, the concentration of the histamine releaser and certain structural properties of histamine releasers that can cause aggregation of the histamine releaser in solution and in the blood upon intravenous administration to an animal.

It is now believed that histamine release may be related to the initial bolus concentration of the histamine releaser, and that the critical events leading to histamine release take place very soon after the injection. Slowing the rate of injection effectively lowers the concentration of the histamine releaser since intravenously injected histamine releasers are diluted by the flow of blood that passes the injection site while the agent is being injected.

By studying surface tension properties of histamine releasers, it has been found that certain histamine releasers tend to self-associate, or aggregate in aqueous solution. It is now believed that this aggregation of the histamine releaser triggers the histamine release. We have identified structural properties shared by the various histamine releasers, which may cause aggregation.

The histamine releasers referred to in the present invention all share the common structural features of one or more hydrophilic portions distanced from one or more hydrophobic portions. For example, neuromuscular blockers are bis-quaternary ammonium salts which possess two cationic charges at the ends of the molecule, separated by a hydrophobic, lipophilic linker. In the case of non-steroidal (e.g., benzylisoquinoline-type) neuromuscular blockers, the hydrophobic linker is typically long and flexible. In the case of steroidal neuromuscular blockers, the hydrophobic linker may be bulky and/or rigid.

Because of this structural characteristic, the histamine releasers are soluble in both water and organic solvents. The structural and solubility characteristics of histamine releasers are similar to surfactants and detergents. Surfactants and detergents are known to aggregate in solution in a concentration dependent manner. The presence of a charged hydrophilic portion distanced from a hydrophobic portion of a molecule may impose on the histamine releaser a tendency to self-solvate or aggregate in solution just as a detergent or surfactant, thus explaining the observation of surface tension modifying properties of the histamine releasers.

Our studies indicate that histamine releasers may aggregate in solution. Possible arrangements of aggregates in solution include but are not limited to dimers, trimers, micelles, rods, plates and sheets. In general, histamine releasers tend to aggregate in arrangements which seek to isolate the hydrophobic portion(s) of the molecule from the aqueous solution in which it is dissolved. This can be accomplished, for example, by forming micelles wherein the hydrophobic portion of the histamine releaser molecule is oriented toward the center of the micelle and the charged hydrophilic portion of the molecule is oriented outward from the center of the micelle. For example, the molecules of a neuromuscular blocker could bend in the region of the hydrophobic portion allowing multiple molecules to aggregate by positioning the hydrophobic portion of each molecule in proximity to the hydrophobic portions of other molecules, while extending the cationic, hydrophilic portion outward. This aggregated arrangement of neuromuscular blocker molecules results in aggregation with poly-cationic surfaces extending outward from the center of the aggregate. It has been found that the degree of aggregation is concentration dependent, such that higher concentrations of histamine releaser result in more aggregation and/or higher order aggregates (e.g., micelles as compared to dimers).

Many pharmaceutical agents, including most neuromuscular blockers are administered intravenously at concentrations in the millimolar (mM) range; a concentration range at which it is likely the drug is partly aggregated and may be near its critical micelle concentration. The "critical micelle concentration" is the concentration at which molecules in a given environment aggregate to form micelles. The critical micelle concentration of a given agent can be measured using the techniques describe herein as well as other conventional techniques, including those described in Anacker, E. W. (1970), MICELLE FORMATION OF CATIONIC SURFACTANTS IN AQUEOUS MEDIA, Cationic Suffactants, E. Jungermann. New York, Marcel Dekker, Inc.; Attwood, D. (1995), Advances in Colloid and Interface Science 55: 271–303; and Mukerjee, P. and K. J. Mysels (1971), CRITICAL MICELLE CONCENTRATIONS IN AQUEOUS SURFACTANT SYSTEMS, Washington, D.C., U.S. Dept. of Commerce, the disclosures of which are incorporated herein by reference.

As is known by those skilled in the art, critical micelle concentration is dependent upon a number of factors. See, Attwood, D. and A. T. Florence (1983), SURFACTANT SYTEMS: THEIR CHEMISTRY, PHARMACY, AND BIOLOGY, London, Chapman and Hall; Rosen, M. J. (1978), SURFACTANTS AND INTERFACIAL PHENOMENA, New York, Wiley-Interscience; Jungermann, E., Ed. (1970), CATIONIC SURFACTANTS, New York, Marcel Dekker, Inc.; and Jonsson, B., B. Lindman, et al. (1998), SURFACTANTS AND POLYMERS IN AQUEOUS SOLUTION, Chichester, John Wilet & Sons (the disclosures of which are incorporated herein by reference) for a discussion of the factors which can effect critical micelle concentration. One such factor is the nature of the solution or suspension in which the aggregates are forming. For example, the data obtained for (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride, an ultra-short acting neuromuscular blocker in water is consistent with a critical micelle concentration at about 15 mg/mL (about 14 mM), while in saline the data obtained for this drug is consistent with a critical micelle concentration at between 40 and 80 mM. The concentration of neuromuscular blockers used clinically typically ranges from about 1 to about 55 mM.

Aggregation of the histamine releaser and the critical micelle concentration are highly dependent on many factors. One factor is the structure of the particular histamine releaser molecule, including the presence and structure of one or more hydrophobic domains distanced from one or more hydrophilic domains that often contain cationic or anionic groups. In addition, aggregation and critical micelle concentration are highly dependent on the concentration of the histamine releaser in solution, the presence and concentration of other molecules in solution, pH, the identity and valency of the counter-ion to any cationic or anionic groups, and on the temperature and pressure of the solution.

Upon injection of the histamine releasers into blood, the resultant new solution (i.e., the solution of histamine releaser in blood) is believed to change many of the factors listed above very rapidly. Given the rapidly changing solution conditions such as the ionic composition of blood and the presence of many other dissolved solutes, cells, proteins, etc., it is reasonable to expect these conditions would favor increased aggregation and/or a lower critical micelle concentration. Overall, it is likely that these histamine releasers are already highly aggregated in the formulation being administered and that the physical act of mixing with blood in the vein upon injection may favor increased aggregation and/or the formation of micelles.

Aggregated histamine releaser molecules are now believed to induce histamine release from cells, tissues and fluids in essentially the same manner as aggregated molecules of surfactants. Aggregated molecules of surfactants can cause a detergent action that can solubilize organic molecules in water, extract proteins from membranes, and cause cell membranes to become permeable. Increasing the permeability of the membrane makes it easier for molecules to enter the cell, and for molecules in the cell, such as histamine molecules, to be released.

It has now been observed that histamine releasers tend to aggregate. These aggregates may exhibit detergent-like properties. Accordingly, it is believed that the detergent-like properties of the aggregated histamine releaser may cause cell membranes to become disturbed possibly to the point that the cells rupture. The disturbance of cellular membranes of histamine containing cells, or in tissues or fluids and/or rupture of these cells may cause the release of intracellular components and molecules into the surrounding environment. Surfactants and detergents are known to cause the release of histamine by rupturing the cell membrane of mast cells, which are known to store and release histamine. Other cell types may behave similarly. For example, basophils present in blood are also known to store and release histamine and would be expected to behave similar to mast cells when exposed to a surfactant or aggregated histamine releaser.

Even lower order aggregates (i.e., dimers and trimers) may cause histamine release that may or may not be related to detergent-like effects. See, Read, G. W. and J. F. Lenney, *Journal of Medicinal Chemistry* 15(3): p. 320–23 (1972).

For example, because bis-cationic agents such as neuromuscular blockers, carry two ammonium groups per molecule, it is currently expected that histamine releasing effects can be expected when as few as 2–4 molecules of neuromuscular blocker aggregate.

In addition to this direct mechanism explaining the release of histamine, it is also possible that histamine release can be caused by indirect mechanisms. Cells that do not store histamine, such as endothelial cells lining blood vessels, may cause the release of histamine by an indirect mechanism. Aggregates of histamine releasers may cause the release of cellular components from endothelial cells (or other cells which do not store histamine), and those components may travel to histamine-containing cells and signal the release of histamine from those storage cells.

III. Methods of Making Formulations

The present invention provides several methods of making pharmaceutical formulations containing a histamine releaser and a physiologically acceptable excipient, which seek to address the above mentioned tendencies of histamine releasers to aggregate and cause the release of undesirable levels of histamine upon administration in vivo.

A. Histamine Releasers

In particular, the histamine releasers referred to in the present invention and which are employed in the methods of making pharmaceutical formulations, include anesthetics, opiates, neuromuscular blockers, imaging agents, hormones for diagnostic procedures, tricyclic glycopeptide antibiotics, cephalosporin antibiotics, penicillin and penicillin derivative antibiotics, intravenously administered non-steroidal anti-inflammatory agents (NSAIDs), anticoagulants, ACE inhibitors, and benzodiazepine receptor antagonists, which have the structural features noted above in the definition of the "histamine releaser." Preferably, the histamine releaser is selected from the group consisting of anesthetics, opiates, neuromuscular blockers, and imaging agents. More preferably the histamine releaser is a neuromuscular blocker.

Examples of anesthetics include but are not limited to thiopental and thiobutabarbital. Examples of opiates include but are not limited to morphine, morpholinic derivatives such as oxymorphone, nalbuphine hydrochloride, buprenorphine, hydromorphone, fentanil and fentanil derivatives including remifentanil, sufentanil and alfentanil. Examples of neuromuscular blockers include but are not limited to non-steroidal neuromuscular blocking agents such as (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride (hereinafter sometimes referred to as "Compound 1" for the sake of brevity), mivacurium, atracurium, d-tubocurarine, metocurine, doxacurium, and gallamine; steroidal neuromuscular blocking agents such as vecuronium, pancuronium, rocuronium, and rapacuronium; and other neuromuscular blockers such as succinylcholine. Examples of imaging agents include but are not limited to ioxaglic (ioxaglate) acid and diatrizoate sodium.

Pharmaceutically acceptable salts of any of the foregoing are also contemplated by the present invention. Thus, the present invention contemplates the use of atracurium besylate, mivacurium chloride, vecuronium bromide, pancuronium bromide, rapacuronium bromide, doxacurium chloride, succinylcholine chloride, morphine sulphate, hydromorphone hydrochloride, pharmaceutically acceptable salts of Compound 1, and the like.

Combinations of any two or more of the above-referenced histamine releasers into a single formulation are also contemplated, provided that the two or more histamine releasers do not react in a manner which deleteriously impacts their therapeutic activity.

Preferred histamine releasers for use in the present invention include morphine, Compound 1, mivacurium, atracurium, vecuronium, pancuronium, rocuronium, rapacuronium, and succinylcholine chloride and pharmaceutically acceptable salts thereof. Compound 1 and pharmaceutical formulations and methods of treatment using this compound are described in PCT Publication Nos. 98/42674 and 98/42675, both published Oct. 1, 1998, to Glaxo Wellcome Inc. and Cornell Research Foundation, the subject matter of which are hereby incorporated by reference in their entirety.

In one preferred embodiment, the histamine releaser is Compound 1 or a pharmaceutically acceptable salt thereof. In one preferred embodiment, the histamine releaser is mivacurium or a pharmaceutically acceptable salt thereof. In one preferred embodiment, the histamine releaser is atracurium or a pharmaceutically acceptable salt thereof, e.g., atracurium besylate.

B. Physiologically Acceptable Excipients

According to the methods of the present invention the histamine releaser is combined with a physiologically acceptable excipient, which may be a single physiologically acceptable excipient or a combination of two, three or more physiologically acceptable excipients. "Excipient" as used herein means both a single physiologically acceptable excipient and a combination of two, three or more physiologically acceptable excipients.

Preferred excipients are those which are conventionally employed in approved parenteral or injectable formulations. The excipients employed in the present invention are physically characterized by the presence of charge (e.g., ionic excipients) and/or the presence of organic residues which are capable of affecting the solvation of the histamine releaser. More particularly, the excipients are capable of ionizing in solution and/or may be solvating the histamine releaser or aiding in the salvation of the histamine releaser.

Suitable excipients for use in the present invention may be selected from a variety of categories, including but not limited to divalent inorganic salts (i.e., inorganic salts having a divalent anion, a divalent cation, or both), organic carboxylic acids, phosphoric acid, amino acids, chelating agents, albumins and combinations thereof. Preferred excipients are selected from the group consisting of divalent inorganic salts, organic carboxylic acids, phosphoric acid, amino acids, chelating agents, albumins and combinations thereof. In one embodiment, the excipient is a divalent inorganic salt. In one embodiment, the excipient is an organic acid. In one embodiment, the excipient is a chelating agent. In one embodiment, the excipient is an amino acid.

Examples of suitable divalent inorganic salts include but are not limited to calcium chloride, magnesium sulphate, magnesium chloride, sodium sulphate, and combinations thereof. Calcium chloride is a preferred excipient for use in the present invention.

Examples of suitable organic carboxylic acids include but are not limited to tartaric acid (which includes racemic tartaric acid, D-tartaric acid and L-tartaric acid) maleic acid, acetic acid, citric acid, succinic acid, glucuronic acid, and combinations thereof. "Citric acid" as used herein refers to citric acid and any hydrates and salts thereof, i.e., citrates. Citric acid is a preferred excipient for use in the present invention.

The term "phosphoric acid" as used herein also includes salts of phosphoric acid, such as sodium phosphate. As will be readily apparent to one skilled in the art, the use of phosphoric acid as an excipient in the instant invention will require that it be provided in a concentration which is physiologically acceptable.

Examples of suitable amino acids include but are not limited to glycine, lysine, arginine and combinations thereof. Glycine is a preferred excipient for use in the present invention.

Examples of suitable chelating agents include but are not limited to ethylene diamine tetracetic acid (EDTA), salts of EDTA (including EDTA-disodium and EDTA-calcium disodium) and combinations thereof. "EDTA" as used herein, shall refer to EDTA and any salts thereof. EDTA is a preferred excipient for use in the present invention.

Examples of suitable albumins include bovine serum albumin, human serum albumin and combinations thereof.

One skilled in the art will appreciate that additional excipients may be employed, which exhibit the physical characteristics noted above and which are capable of reducing aggregation of the histamine releaser in aqueous solution and/or otherwise suppressing pharmaceutically-induced histamine release. Such other excipients may be ascertained by utilizing the techniques described below regarding the determination of appropriate excipient concentrations for use in the present invention, and are therefore contemplated by the present invention.

The excipient may be a combination of any two, three, or more excipients all selected from one of the foregoing categories, or a combination of any two, three or more excipients selected from two or more different categories above. For example, the excipient may be a combination of a divalent inorganic salt and an organic carboxylic acid. In another embodiment, the excipient may be an organic carboxylic acid and a chelating agent. In another embodiment, the excipient may be a combination of a divalent inorganic salt and a chelating agent. In yet another embodiment, the excipient may be a combination of a divalent inorganic salt, an organic carboxylic acid and a chelating agent. In yet another embodiment, the excipient may be a combination of a divalent inorganic salt and an amino acid.

The only requirement for utilizing combinations of excipients in the methods and formulations of the present invention is that the selected excipients will not interact with each other in a manner which is deleterious to their ability to function in the methods and formulations of the present invention. Other combinations of two or more physiologically acceptable excipients will be readily apparent to those skilled in the art based upon the foregoing examples, and are contemplated by the instant invention. The techniques described below for the determination of appropriate excipient concentrations are equally applicable for the determination of various other combinations of two, three or more excipients which can be employed in the present invention.

In one preferred embodiment, the excipient is a combination of any two or more (i.e., two, three or all four) excipients selected from the group consisting of glycine, EDTA, citric acid and calcium chloride. In one preferred embodiment, the excipient is a combination of citric acid and EDTA. In one preferred embodiment, the excipient is a combination of citric acid and calcium chloride. In one preferred embodiment, the excipient is a combination of glycine and EDTA. In one preferred embodiment, the excipient is a combination of glycine and citric acid. In one preferred embodiment, the excipient is a combination of citric acid, glycine and calcium chloride.

C. Methods for Determining a Suitable Concentration of Excipient

According to the methods of the present invention, pharmaceutical formulations are prepared by combining a therapeutically effective amount of the histamine releaser with a concentration of the physiologically acceptable excipient. Preferred excipients for use in these methods of the present invention may be selected from the group consisting of divalent inorganic salts, organic carboxylic acids, phosphoric acid, amino acids, chelating agents, albumins and combinations thereof. In general, the concentration of the excipient is a concentration which is sufficient to suppress pharmaceutically-induced histamine release in an animal being treated with a histamine releaser. In one embodiment, the concentration of the excipient is a concentration which when combined in an aqueous solution with the histamine releaser at or above the critical micelle concentration of the histamine releaser, is sufficient to reduce aggregation of the histamine releaser in the aqueous solution by at least about 25 percent compared to aggregation of the histamine releaser at the same concentration in the aqueous solution containing substantially no excipient.

"Substantially no excipient" means that the solution or mixture is substantially free of excipient, that is, it does not contain an amount of excipient that is sufficient to reduce aggregation of the histamine releaser in solution or suppress pharmaceutically-induced histamine release in vitro or in vivo. Preferably, "substantially no excipient" means that the solution or mixture does not contain an amount of excipient that is sufficient to either reduce aggregation of the histamine releaser by more than 10 percent or suppress pharmaceutically-induced histamine release in vitro or in vivo, by more than 5 percent.

In other words, in an aqueous solution containing the histamine releaser at or above its critical micelle concentration and one or more physiologically acceptable excipients in suitable concentrations, aggregation of the histamine releaser will be at least about 25 percent lower than aggregation of the histamine releaser in an aqueous solution containing substantially the same concentration of histamine releaser and substantially no physiologically acceptable excipient. The inclusion of the physiologically acceptable excipient in the solution containing the histamine releaser substantially reduces aggregation of the histamine releaser in the solution.

"Reduce(d) aggregation," "lower(ed) aggregation" or "decrease(d) aggregation" refers to a decrease in average aggregate size (which can be a function of conformation of the molecules or aggregates or the number of molecules forming the aggregate) and/or a decrease in the number of aggregates per unit volume. Methods for measuring aggregation of the histamine releaser and thereby identifying a concentration of excipient which is suitable for preparing the formulations of the present invention, are discussed below. Preferably, the concentration of the excipient will be a concentration which is sufficient, for the particular histamine releaser and excipient employed, to reduce aggregation of the histamine releaser in the aqueous solution by at least about 50 percent, and more preferably by at least about 60 percent, as compared to an aqueous solution of histamine releaser containing substantially no excipients.

In another embodiment, the concentration of the excipient is a concentration which is sufficient to substantially reduce histamine release from a histamine-containing biological sample in a mixture of the histamine-containing biological sample in medium and an aqueous solution containing both the histamine releaser in a concentration sufficient to cause histamine releaser from the biological sample and the physiologically acceptable excipient, compared to histamine release from the histamine-containing biological sample in a mixture consisting of the histamine-containing biological sample in medium, and an aqueous solution containing substantially the same concentration of the histamine releaser, and substantially no excipient. That is, histamine release from the biological sample is reduced by at least about 10 percent compared to the reference mixture which contains substantially no excipient.

In other words, a mixture of the histamine containing-biological sample in medium and an aqueous solution containing the histamine releaser at a concentration sufficient to cause histamine release from the histamine-containing biological sample and the physiologically acceptable excipient in a suitable concentration, will exhibit histamine release from the histamine-containing biological sample, which is at least about 10 percent lower than histamine release from a histamine-containing biological sample in a mixture of the histamine-containing biological sample in medium and an aqueous solution containing the same concentration of histamine releaser and substantially no physiologically acceptable excipient. Methods for measuring histamine release from the histamine-containing biological sample and methods for identifying a concentration of excipient which is suitable for preparing the formulations of the present invention based upon the measured histamine release from the histamine-containing biological sample, are discussed further below. Preferably, the concentration of the excipient will be a concentration which is sufficient, for the particular histamine releaser and excipient employed, to reduce histamine release from the histamine-containing biological sample by at least about 20 percent and more preferably by at least about 25 percent, as compared to histamine release from the histamine-containing biological sample in a mixture consisting of the histamine-containing biological sample in medium, and an aqueous solution containing the histamine releaser at substantially the same concentration and substantially no excipient.

In yet another embodiment, the concentration of the excipient is a concentration which, when intravenously administered together with a histamine releaser to an animal, is sufficient to suppress one or more of the physical manifestations of plasma and/or tissue concentrations of histamine that are above normal physiological levels of histamine. The suppression of one or more physical manifestations of plasma and/or tissue concentrations of histamine above normal physiological levels can be observed qualitatively or quantitatively, and is discussed further below.

The present invention provides multiple methods for determining a concentration of excipient which is suitable for combining with the histamine releaser to prepare the pharmaceutical formulations of the present invention. A suitable concentration of excipient employed in the present invention will depend upon various factors including for example, the particular histamine releaser with which the excipient will be combined, the animal which is being treated with the histamine releaser or to which the pharmaceutical formulation will be administered, and the particular excipient (or combination of excipients) employed. In some cases, pH may play a role in the optimization of the concentration of excipients as well. In general, the suitable concentration of the excipient will be a physiologically acceptable concentration.

1.) Solution-Based Methods

According to one method of the present invention, the concentration of excipient is determined by the method comprising the steps of: a) measuring aggregation of the histamine releaser in a reference solution consisting essentially of the histamine releaser in a concentration at or above the critical micelle concentration in the aqueous solution; b) measuring aggregation of the histamine releaser in a comparative solution consisting essentially of the histamine releaser and a pre-selected concentration of the physiologically acceptable excipient in the aqueous solution, wherein the concentration of the histamine releaser in the comparative solution is substantially the same as the concentration of the histamine releaser in the reference solution; c) optionally repeating step b) one or more times with a comparative solution having a different pre-selected concentration of the physiologically acceptable excipient; d) identifying a concentration of physiologically acceptable excipient that is sufficient to reduce aggregation of the histamine releaser in the comparative solution by at least about 25 percent compared to aggregation of the histamine releaser in the reference solution. The identified concentration of step d) is the concentration of the physiologically acceptable excipient for combining with the histamine releaser to prepare the pharmaceutical formulation.

The order of steps a), b) and c) is not critical. These steps may be carried out in any desired order, as will be appreciated by those skilled in the art. It is not necessary that the aggregation of the histamine releaser in the reference solution be measured before aggregation of the histamine releaser in the comparative solution, and the present invention contemplates methods comprising these steps in any suitable order.

Step c) of optionally, repeating step b) one or more times means that step b) may be repeated with multiple comparative solutions, but is not required. One skilled in the art is capable of determining whether it is desirable in a particular case to carry out step c), (i.e., repeat step b)) or not. In general, the preferred methods of the invention include repeating step b) at least once, and more preferably more than once.

The reference solution and comparative solution(s) can be prepared using conventional techniques. For example, the reference solution can be prepared by solubilizing the histamine releaser, at or above the critical micelle concentration of the histamine releaser, in aqueous solution.

One or more comparative solution(s), each including a different pre-selected concentration of excipient, can be prepared according to several different methods. Each comparative solution, after addition of the pre-selected concentration of excipient, will have a histamine releaser concentration which is substantially the same as the concentration of the histamine releaser in the reference solution. "Substantially the same" concentration means that the difference in the concentration of the histamine releaser between the reference solution and the comparative solution is not sufficient to produce a measurable effect on aggregation of the histamine releaser. More preferably, the concentration of the histamine releaser in the comparative solution(s) will be considered to be substantially the same as the concentration in the reference solution when the concentration of the comparative solution(s) is the concentration of the reference solution plus or minus about 5%. For the most informative comparison of the aggregation of the histamine releaser in the reference solution versus aggregation of the histamine releaser in the comparative solution, each of the reference solution and the comparative solution(s) will contain an equivalent concentration of histamine releaser.

According to one embodiment, comparative solution(s) are prepared by titrating pre-selected, or otherwise known, concentrations of the excipient into an aqueous solution containing the appropriate concentration of the histamine releaser. The excipient may be titrated into the solution containing the histamine releaser by titrating either up or down, according to techniques known to those skilled in the art. Thus, the present invention provides a method for determining a suitable concentration of excipient for combining with the histamine releaser to prepare a pharmaceutical formulation that comprises the steps of: 1) measuring aggregation of the histamine releaser in a reference solution consisting essentially of the histamine releaser at or above critical micelle concentration in the aqueous solution; 2) titrating the physiologically acceptable excipient into the reference solution, to prepare comparative solutions; and 3) identifying a concentration of physiologically acceptable excipient sufficient to reduce aggregation of the histamine releaser in the comparative solution by at least about 25 percent compared to the measured aggregation of step 1). The identified concentration is the concentration of the physiologically acceptable excipient for combining with the histamine releaser to prepare the pharmaceutical formulation. The step of "titrating the excipient" refers to incrementally adding known quantities of excipient (or diluting down to known quantities of excipient) while monitoring the aggregation of the histamine releaser in the solution.

According to another embodiment, comparative solution(s) are prepared by solubilizing a pre-selected concentration of excipient in aqueous solution to create a stock solution having the highest concentration of excipient, diluting a portion of the stock solution by a suitable dilution factor (e.g., serially diluting the stock solution) one or more times to prepare multiple aqueous solutions of excipient each containing a pre-selected concentration of excipient, and then solubilizing the appropriate amount of histamine releaser in each prepared aqueous solution of excipient to obtain one or more comparative solutions each having a histamine releaser concentration substantially the same as the concentration of histamine releaser in the reference solution.

Comparative solutions containing differing concentrations of a combination of two or more excipients may be utilized in the methods of the present invention just as comparative solutions containing differing concentrations of only one excipient. It is well within the purview of one skilled in the art to prepare multiple comparative solutions, each containing a different pre-selected concentration of two or more different excipients. For example, this can be accomplished by preparing multiple different comparative solutions each having a different concentration of only one of the two or more excipients while the concentration of the other(s) excipients remain constant. Alternatively, multiple different comparative solutions can be prepared, each having a different concentration of more than one, or even all of the excipients. When the excipient employed in the methods and formulations of the present invention is a combination of two or more excipients, all that is required is that the concentration of each of the two or more excipients in each comparative solution should be known.

Steps a) and b) of measuring aggregation of the histamine releaser in the reference solution and the comparative solution(s), can be carried out in many different ways. Advantageously, aggregation can be measured using conventional equipment and techniques known to those skilled in the art.

(a) Surface Tension Analysis

According to one technique, steps a) and b) are carried out by measuring aggregation of the histamine releaser in aqueous solution using surface tension analysis. Methods of measuring aggregation by surface tension are generally described in Anacker, E. W. (1970), MICELLE FORMATION OF CATIONIC SURFACTANTS IN AQUEOUS MEDIA, *CATIONIC SURFACTANTS*, E. Jungermann. New York, Marcel Dekker, Inc.; Iwunze, M. O., M. Lambert, et al. (1997), *Monatshefte fur Chemie* 128: 582–592; Attwood, D. and R. Natarajan (1979), *J. Pharm. Pharmacology* 32: 460–462; Moroi, Y. and et.al. (1990), *Journal of Physical Chemistry* 94: 842–845; and Rosen, M. J., J. H. Mathias, et al. (1999), *Langmuir* 15(21): 7340–7346, the disclosures of which are incorporated herein by reference in their entirety.

When measuring aggregation by surface tension analysis, the aqueous solution is preferably water (including deuterated water) which may be pH adjusted with hydrochloric acid or sodium hydroxide as may be necessary or desirable to physically and/or chemically stabilize or facilitate the solubilization of certain histamine releasers in the aqueous solution sufficiently long to permit the measurement of aggregation of the histamine releaser using surface tension analysis. Because the surface tension of most liquids decreases with an increase in temperature, it is necessary to control the temperature of the system while evaluating the surface tension of the reference solution and the comparative solution(s).

Aggregation of the histamine releaser in the reference solution and the comparative solution(s) can be measured by measuring the surface tension of each of the reference solution and the comparative solution(s) using the DuNouy ring method, as described in PHYSICAL PHARMACY: PHYSICAL CHEMICAL PRINCIPLES IN THE PHARMACEUTICAL SCIENCES, Editors: Alfred Martin, James Swarbrick, Arthur Cammarata, Third Edition, Lea Et Febiger, Philadelphia, 1983. Surface tension may provide a measure of the critical micelle concentration of the histamine releaser in solution and for this reason is an indicator of aggregation of the histamine releaser in the solution. The critical micelle concentration of the histamine releaser in a solution can be identified by measuring the surface tension of solutions containing increasing concentrations of histamine releaser and observing on a plot of surface tension (y-axis) versus concentration of histamine releaser (x-axis), the point at which an increased concentration of histamine releaser produces substantially the same or even lower surface tension than the surface tension of the preceding lower concentration of histamine releaser. FIG. 1 is a plot of the surface tension of solutions containing the histamine releaser, Compound 1, versus increasing concentration of the Compound 1. The data is consistent with a critical micelle concentration at approximately 15 mg/mL of Compound 1.

It is known that surface tension of a solution containing a compound or material which aggregates will generally decrease as the concentration of the compound or material in solution increases due to adsorption of the compound or material in solution at the surface of the solution. Thus, as increasing concentrations of histamine releaser are added to an aqueous solution, the surface tension of the solution will tend to decrease because of increasing adsorption of the histamine releaser at the surface of the solution up to the point where the surface is saturated. Further addition of the histamine releaser to the solution will result in the formation of aggregates in the bulk solution. It is over a relatively narrow concentration range where this aggregation or micelle formation occurs and this is the critical micelle concentration.

A plot of the surface tension of comparative solutions containing a constant concentration of histamine releaser and various, typically increasing, concentrations of the excipient will enable observation of an end to or a reversal of the surface tension lowering trend or a shift in the critical micelle concentration of the histamine releaser. An end to the surface tension lowering trend can be graphically observed by a change in slope in the plot of surface tension v. concentration. A reversal of the surface tension lowering trend can be graphically observed by a change in direction of the plot of surface tension v. concentration. The end in or reversal of the surface tension lowering trend indicates a reduction in the adsorption of the histamine releaser to the surface of the solution in the comparative solution as compared to the adsorption of the histamine releaser to the surface of the solution in the reference solution. This reduction in turn correlates to a reduction of aggregation of the histamine releaser in solution.

A shift in the critical micelle concentration of the histamine releaser in the comparative solution(s) is another means of identifying a reduction in the aggregation of the histamine releaser by surface tension analysis. A shift in the critical micelle concentration of the histamine releaser in the comparative solution is identified by the observation of a higher critical micelle concentration for the histamine releaser in the comparative solution as compared to the critical micelle concentration of the histamine releaser in the reference solution. Thus, a reduction in aggregation can be identified by observing a critical micelle concentration of the histamine releaser in the comparative solution occurring at a higher concentration of histamine releaser than the critical micelle concentration of the histamine releaser in the reference solution which contains substantially no physiologically acceptable excipient.

For purposes of comparing aggregation of the histamine releaser in the reference solution to aggregation of the histamine releaser in the comparative solution(s), the surface tension properties of the solutions can be observed as a plot or curve of surface tension (y-axis) versus concentration of excipient (x-axis). The reference solution and the comparative solution(s) each represent one point on the surface tension versus concentration curve. In this manner, trends in the surface tension of the solutions as the concentration of excipient is altered (i.e., raised or lowered) can be readily observed.

(b) NMR Methods

According to another technique, steps a) and b) are carried out by measuring aggregation of the histamine releaser in aqueous solution using nuclear magnetic resonance spectroscopy (NMR). Methods of measuring aggregation by NMR are described in Wiedmer, S. K., M. L. Riekkola, et al. (1997), *Analytical Chemistry* 69(8): 1577–1584 and Jonsson, B., B. Lindman, et al. (1998), SURFACTANTS AND POLYMERS IN AQUEOUS SOLUTION. Chichester, John Wilet & Sons, the discloures of which are incorporated herein by reference in their entirety.

Proton NMR spectra of the histamine releaser in aqueous solution can be measured using conventional techniques known to those skilled in the art of NMR spectroscopy on a conventional NMR spectrometer. Based upon the spectra obtained, chemical shift changes (See, Y. S. Lee, et al., *Bull. Korean Chem. Soc.,* 1993, 14(3), 392–398) line width changes (See, J. H. Bradbury, et al., *Nature,* 1968, 218, 1049–1050; L. Hwang, et al., *J. Phys. Chem.,* 1988, 92, 4753–4758), relaxation ($T_1$ and $T_2$ relaxation rate constants) (See, Y. S. Lee, et al., *Bull. Korean Chem. Soc.,* 1993, 14(3), 392–398; B. P. Hills, et al., *Macromolecules,* 1991, 24, 2944–2950), and diffusion coefficients (See, K. F. Morris, et al., *JACS,* 1993, 115, 4291–4299; P. Stilbs, *Prog. Nucl. Magn. Reson. Spectrosc.,* 1987, 19,1–45) can be measured. Typically, aggregation of the histamine releaser in the reference solution and the comparative solution is measured by NMR relaxation.

There are two types of NMR relaxation, spin-lattice and spin-spin relaxation, referred to as $T_1$ and $T_2$ values, respectively. $T_1$ and $T_2$ are rate constants which measure the relaxation of NMR magnetization back to equilibrium (hereinafter collectively referred to as "NMR relaxation rates"). For small molecules in what is called the extreme narrowing limit, both $T_1$ and $T_2$ increase in inverse proportion to the rotational tumbling rate $t_c$, which, in turn, is directly proportional to the average size of the aggregate. Thus, for small molecules, increases in $T_1$ and/or $T_2$ rates with the addition of excipient to the solution containing the histamine releaser, in the absence of significant changes in the viscosity of the solution, indicates a decrease in aggregation.

According to one embodiment, the steps a) and b) of measuring aggregation of the histamine releaser in the reference solution and comparative solution(s) comprise measuring proton NMR relaxation rates of the histamine releaser in the reference solution and the comparative solution.

The aggregation of the histamine releaser in each comparative solution is measured and compared to the measure of aggregation of the histamine releaser in the reference solution. Comparison to the measure of aggregation of the histamine releaser in the reference solution will enable the ready identification of the comparative solution(s), which exhibit a measure of aggregation of the histamine releaser which is at least about 25 percent lower than the measure of aggregation of the histamine releaser in the reference solution. The step of identifying the concentration of physiologically acceptable excipient which is sufficient to reduce aggregation of the histamine releaser in the comparative solution(s) by at least about 25 percent compared to aggregation of the histamine releaser in the reference solution may be achieved after comparing the measured aggregation of the histamine releaser in each of the reference solution and the comparative solution(s), as the concentration of excipient in each comparative solution is pre-selected or known. Thus, in one embodiment of the method for determining the concentration of excipient, step d) of identifying a concentration of physiologically acceptable excipient that is sufficient to reduce aggregation of the histamine releaser in the comparative solution by at least about 25 percent compared to the measured aggregation of the histamine releaser in the reference solution, comprises identifying a concentration of physiologically acceptable excipient sufficient to slow the measured NMR relaxation rates of the histamine releaser in the comparative solution by at least about 25 percent, more preferably about 50 percent and most preferably about 60 percent, compared to the measured NMR relaxation rates of the histamine releaser in the reference solution. A longer time in seconds for the measured $T_1$ and $T_2$ values, is indicative of a slower relaxation rate. As will be apparent to those skilled in the art, viscosity changes should be taken into account when measuring aggregation with relaxation rates.

Carbon-13 nuclear magnetic resonance may also be used in steps a) and b) to measure aggregation of the reference solution and comparative solution(s) in order to determine concentrations of excipient that are suitable for preparation of the pharmaceutical formulations of the invention. This method involves measuring the relaxation rates or chemical shifts changes for carbon rather than proton and has an advantage in that carbon relaxation is typically less complicated than proton relaxation and thus is often easier to interpret. However, it is noted that $^{13}$C-NMR is 100 times less sensitive than $^{1}$H-NMR. In addition, the measurements can be made for other NMR-active nuclei (i.e. $^{31}$P, $^{19}$F) if the structure of the histamine releaser contains these nuclei. The foregoing methods of preparing solutions, measuring aggregation and identifying the concentration of excipient suitable for use in the pharmaceutical formulations of the invention are equally applicable to $^{13}$C-NMR and for other NMR-active nuclei.

As noted above, diffusion coefficients can also be measured by NMR and can provide another measure of aggregation in addition to or instead of the relaxation rate measure discussed above. Diffusion coefficients reflect changes in average aggregate size and/or the number of aggregates and therefore are a meaningful measure of aggregation of the histamine releaser in the reference solution and the comparative solution(s). As will be apparent to those skilled in the art, viscosity changes should be taken into account when measuring aggregation with diffusion coefficients.

The foregoing methods for measuring aggregation of the histamine releaser in the reference solution and the comparative solution(s) and identifying a concentration of excipient which is sufficient to reduce aggregation by at least about 25 percent are illustrative of the methods of the present invention, but are not exhaustive of all possible ways of performing this method of the present invention. One skilled in the art will readily appreciate the many ways that aggregation of the histamine releaser may be measured, as the foregoing examples demonstrate that any suitable technique for measuring aggregation of a molecule in solution will be useful in the methods of the present invention for measuring aggregation of a histamine releaser as well. Additional methods (and references describing such methods) for measuring aggregation include the following, which are incorporated herein by reference:

interfacial tension (see, Rosen, M. J., J. H. Mathias, et al. (1999), *Langmuir* 15(21): 7340–7346);

light scattering (see, Anacker, E. W. (1970), MICELLE FORMATION OF CATIONIC SURFACTANTS IN AQUEOUS MEDIA. *CATIONIC SURFACTANTS*, E. Jungermann, New York, Marcel Dekker, Inc.; Attwood, D. and R. Natarajan (1979), *J. Pharm. Pharmacology* 32: 460–462; Moroi, Y. et.al. (1990), *Journal of Physical Chemistry* 94: 842–845; Moroi, Y., Y. Murata, et al. (1992), *Journal of Physical Chemistry* 96: 8610–13; and Rosen, M. J. (1978), SURFACTANTS AND INTERFACIAL PHENOMENA, New York, Wiley-Interscience);

conductivity (see, Anacker (1970) supra; Attwood, D. and R. Natarajan (1979), supra; Moroi, Y., Y. Murata, et al. (1992), supra; Streng, W. H., D. H. -S. Yu, et al. (1996), *International Journal of Pharmaceutics* 135: 43–52; Iwunze, M. O., M. Lambert, et al. (1997), *Monatshefte fur Chemie* 128: 582–592; Wiedmer, S. K., M. L. Riekkola, et al. (1997), *Analytical Chemistry* 69(8): 1577–1584; and Rosen (1978) supra);

calorimetry (see, Paula, S., W. Sus, et al. (1995), *Journal of Physical Chemistry* 99(30): 11742–11751; Streng, Yu et al. (1996) supra; and Cooper, A., M. A. Nutley, et al. (1998), *Analytical Chemistry* 70(23): 5024–5028);

ultracentrifugation (see, Anacker (1970) supra; and and Rosen (1978) supra);

diffusion measurments (see, Anacker (1970) supra; and Jonsson, B., B. Lindman, et al. (1998), SURFACTANTS AND POLYMERS IN AQUEOUS SOLUTION, Chichester, John Wiley & Sons);

ultrasonic spectroscopy, densitometry, elastic and quasielastic light scattering, and small angle neutron scattering, and Brilloin light scattering (see, D'Arrigo, G., F. Mallamace, et al. (1991), *Physical Review A* 44(4): 2578–2587; and Rosen (1978) supra);

viscosity measurements (see, Anacker (1970) supra);

refractive index (see, Anacker (1970) supra; Moroi, Y. et.al. (1990), supra; Moroi, Y., Y. Murata, et al. (1992), supra; and Rosen (1978) supra);

x-ray diffraction (see, Anacker (1970) supra);

dye solubilization (see, Anacker (1970) supra; and Rosen (1978) supra);

fluorescent spectroscopy (see, Iwunze (1997) supra; Rosen (1978) supra; and Jonsson (1998) supra);

capillary electrophoresis (see, Wiedmer (1997) supra);

potentiometry, spectrophotometry, and kinetic methods (see, Kopecky, F., *Pharmazie* 51(3):135–144 (1996);

osmometry (see, Streng, W. H. et al. (1996) supra; and Rosen (1978) supra); and microscopy, optical and non-optical techniques (see, Binks, B. P., Ed. (1999), *Modern Characterization Methods of Surfactants Systems*, SURFACTANTS SCIENCE SERIES, New York, Marcel Dekker). The disclosures of these references as they pertain to methods of measuring aggregation, are hereby incorporated by reference.

The present invention contemplates, but is not limited by these specific examples of techniques for measuring aggregation, and is defined solely by the claims with other suitable methods of measuring aggregation being contemplated by the present invention.

The foregoing methods for determining a concentration of excipient for combining with the histamine releaser to prepare a pharmaceutical formulation are equally applicable to the determination of a concentration of physiologically acceptable excipient which is sufficient to suppress pharmaceutically-induced histamine release from an animal being treated with a histamine releaser. Thus, the present invention provides a method for determining a concentration of a physiologically acceptable excipient that is sufficient to suppress pharmaceutically-induced histamine release in an animal being treated with a histamine releaser. The method comprises: a) measuring aggregation of the histamine releaser in a reference solution consisting essentially of the histamine releaser in a concentration at or above the critical micelle concentration in an aqueous solution; b) measuring aggregation of the histamine releaser in a comparative solution consisting essentially of the histamine releaser and a pre-selected concentration of the physiologically acceptable excipient in the aqueous solution, wherein the concentration of the histamine releaser in the comparative solution is substantially the same as the concentration of the histamine releaser in the reference solution; c) optionally repeating step b) one or more times with a comparative solution having a different pre-selected concentration of the physiologically acceptable excipient; d) identifying a concentration of physiologically acceptable excipient that is sufficient to reduce aggregation of the histamine releaser in the comparative solution by at least about 25 percent compared to aggregation of the histamine releaser in the reference solution. The identified concentration of step d) is the concentration of the physiologically acceptable excipient that is sufficient to suppress pharmaceutically-induced histamine release in an animal being treated with a histamine releaser. The suppression of pharmaceutically-induced histamine release is discussed further below. The foregoing surface tension and NMR techniques for carrying out the method of determining a concentration of excipient for combining with the histamine releaser to prepare a pharmaceutical formulation method are equally applicable to this method.

2.) In Vitro Methods

According to another method of the present invention, the concentration of excipient is determined by the method comprising the steps of: a) measuring histamine release from a histamine-containing biological sample in a reference mixture consisting essentially of: i) the histamine-containing biological sample in a medium and ii) an aqueous solution of the histamine releaser at a concentration sufficient to cause histamine release from the histamine-containing biological sample; b) measuring histamine release from the histamine-containing biological sample in a comparative mixture consisting essentially of: i) the histamine-containing biological sample in medium and ii) an aqueous solution of the histamine releaser and a pre-selected concentration of the physiologically acceptable excipient, wherein the histamine releaser in the comparative mixture is present in a concentration which is substantially the same as the concentration of histamine releaser in the reference mixture of step a); c) optionally repeating step b) one or more times with a comparative mixture having a different pre-selected concentration of the physiologically acceptable excipient; and d) identifying a concentration of the physiologically acceptable excipient sufficient to reduce histamine release from the histamine-containing biological sample in the comparative mixture by at least about 10 percent compared to histamine release from the histamine-containing biological sample in the reference mixture. The identified concentration of step d) is the concentration of physiologically acceptable excipient for combining with the histamine releaser to prepare the pharmaceutical formulation.

The term "histamine containing biological sample" as used herein includes cell lines, tissues and biological fluids which include cells that contain histamine. Examples of histamine containing biological samples include but are not limited to basophils, mast cells, smooth muscle cells, cardiac myocytes; reperfused lung, skin, blood vessel, heart, brain or gut tissue; and blood and lymph, which biological samples may be from mammals, including humans, rats, dogs, cats, primates (e.g., monkeys), and the like. Preferably, the histamine-containing biological sample is selected from the group consisting of: human, rat, dog or primate blood; human, rat, dog or primate basophil cells; and human, rat, dog or primate mast cells. More preferably, the histamine-containing biological sample is selected from the group consisting of human blood, rat blood, dog blood, rat basophil cells, human mast cells and primate mast cells. The histamine-containing biological sample is hereinafter sometimes referred to as "biological sample" for the sake of brevity.

The biological sample is provided in medium. When the biological sample is cells in culture the medium is the appropriate culture medium. When the biological sample is an isolated tissue or organ in organ bath, the medium is the artificial physiological fluid. When the biological sample is blood the medium is plasma. Thus, a suitable medium will depend upon the particular biological sample employed and will be readily determined by those skilled in the art based upon conventional knowledge.

The order of steps a), b) and c) above is not critical. These steps may be carried out in any desired order, as will be appreciated by those skilled in the art. It is not necessary that histamine release from the biological sample in the reference mixture be measured before histamine release from the biological sample in the comparative solution is measured, and the present invention contemplates methods comprising these steps in any suitable order.

Step c) of optionally, repeating step b) one or more times means that step b) may be repeated with multiple comparative mixtures, but is not required. One skilled in the art is capable of determining whether it is desirable in each particular case to carry out step c) (i.e., repeat step b)) or not. In general, the preferred methods of the invention include repeating step b) at least once, and more preferably more than once.

The reference mixture and comparative mixture(s) can be prepared using conventional techniques. Generally, the reference mixture and comparative mixture(s) are prepared by combining or contacting the biological sample in medium with an aqueous solution. In the case of the reference mixture the aqueous solution contains the histamine releaser at a concentration sufficient to cause measurable histamine release from the biological sample when that concentration of histamine releaser is contacted to or combined with the biological sample in medium. In the case of the comparative mixture(s), the aqueous solution contains the histamine releaser and a pre-selected concentration of the excipient wherein the concentration of the histamine releaser in the aqueous solution, when combined with the biological sample in medium, is sufficient to produce a comparative mixture containing substantially the same concentration of the histamine releaser as in the reference mixture. "Substantially the same" concentration means that the difference in the concentration of the histamine releaser between the reference mixture and the comparative mixture is not sufficient to produce a measurable effect on histamine release from the biological sample. More preferably, the concentration of the histamine releaser in the comparative mixture(s) will be considered to be substantially the same as the concentration in the reference mixture when the concentration of the comparative mixture(s) is the concentration of the reference mixture plus or minus about 5%. For the most informative comparison of the histamine release in the reference mixture versus histamine release in the comparative mixture, each of the reference mixture and the comparative mixture(s) will contain an equivalent concentration of histamine releaser.

A concentration of the histamine releaser which is sufficient to cause histamine release from the biological sample can be determined by contacting one or more pre-selected concentrations of histamine releaser to the biological sample in medium and detecting the presence or absence of histamine release or measuring the amount of histamine released from the biological sample. Methods for detecting the presence or absence of histamine release and methods for measuring the amount of histamine released from the biological sample are discussed further below.

The aqueous solutions for use in the preparation of the reference mixture and the comparative mixture(s) can be prepared using the same general techniques as described above with reference to methods of preparing reference solutions and comparative solutions for analysis of aggregation. For example, the aqueous solution for use in the reference mixture can be prepared by solubilizing or suspending the histamine releaser, at a concentration sufficient to cause histamine release from the biological sample, in the aqueous solution.

One or more aqueous solutions for preparation of one or more comparative mixtures, each including a different pre-selected concentration of excipient, can be prepared according to several different methods. According to one embodiment, aqueous solution(s) for the comparative mixture(s) are prepared by titrating pre-selected, or otherwise known, concentrations of the excipient into an aqueous solution containing the appropriate concentration of the histamine releaser. The excipient may be titrated into the solution containing the histamine releaser by titrating either up or down, according to techniques known to those skilled in the art.

According to another embodiment, aqueous solution(s) for the comparative mixture(s) are prepared by solubilizing a pre-selected concentration of excipient in the aqueous solution to create a stock solution having the highest concentration of excipient, diluting a portion of the stock solution by a suitable dilution factor (e.g., serially diluting the stock solution) one or more times to prepare multiple aqueous solutions of excipient each containing a pre-selected concentration of excipient, and then solubilizing the appropriate amount of histamine releaser in each prepared aqueous solution of excipient so that when the aqueous solutions are combined with the biological sample in medium to prepare the comparative mixture(s), each comparative mixture will have a histamine releaser concentration substantially the same as the concentration of histamine releaser in the reference mixture.

Comparative mixtures containing differing concentrations of a combination of two or more excipients may be utilized in the methods of the present invention just as comparative mixtures containing differing concentrations of only one excipient. It is well within the purview of one skilled in the art to prepare multiple comparative mixtures, each containing a different pre-selected concentration of each of two or more different excipients. For example, this can be accomplished by preparing multiple different comparative mixtures each having a different concentration of only one of the two or more excipients while the concentration of the other excipient(s) remain(s) constant. Alternatively, multiple different comparative mixtures can be prepared, each having a different concentration of more than one, or even all of the excipients. When the excipient employed in the methods and formulations of the present invention is a combination of two or more excipients, all that is required is that the concentration of each of the two or more excipients in each comparative mixture should be known.

Methods of detecting histamine release from the biological sample and methods for carrying out steps a) and b) of measuring histamine release from the biological sample in the reference mixture and the comparative mixture(s), can be carried out using conventional techniques. Examples of conventional techniques for detecting and measuring histamine release from a biological sample include those described in INFLAMMATION: BASIC PRINCIPLES AND CLINICAL CORRELATES (Eds. J. I. Gallin, I. M. Goldstein, and R. Snyderman, Chap. 11, *Measurement of Histamine*, p. 202, Raven Press, New York, 1992, the subject matter of which is already incorporated herein by reference in its entirety. Specifically, in vitro and in vivo enzyme-linked immunosorbent assay (ELISA) methods and radio-immunoassay (RIA) methods and fluorometric assay methods may be employed to detect and measure histamine release from the biological sample. Using ELISA, RIA or fluorometric assay results, the percent inhibition of histamine release from the biological sample can be determined for each of the comparative mixtures relative to histamine release from the biological sample in the reference mixture. Although the foregoing discussion specifically mentions ELISA, RIA and fluorometric assay methods for detecting histamine release, other conventional methods for determining histamine release from a biological sample may be employed.

The step of identifying the concentration(s) of excipients sufficient to reduce the histamine release from the biological sample by at least about 10 percent comprises identifying the pre-selected concentration of the excipient in the comparative mixture(s) which cause the histamine release from the biological sample to be at least about 10 percent lower than the histamine release from the biological sample in the reference mixture. The identified concentration of excipient is the concentration for combining with the histamine releaser to prepare the pharmaceutical formulations of the invention.

The foregoing methods for determining a concentration of excipient for combining with the histamine releaser to prepare a pharmaceutical formulation are equally applicable to the determination of a concentration of physiologically acceptable excipient which is sufficient to suppress pharmaceutically-induced histamine release from an animal being treated with a histamine releaser. Thus, the present invention provides a method for determining a concentration of a physiologically acceptable excipient that is sufficient to suppress pharmaceutically-induced histamine release in an animal being treated with a histamine releaser which method comprises: a) measuring histamine release from a histamine-containing biological sample in a reference mixture consisting essentially of: i) the histamine-containing biological sample in a medium and ii) an aqueous solution of the histamine releaser at a concentration sufficient to cause histamine release from the histamine-containing biological sample; b) measuring histamine release from the histamine-containing biological sample in a comparative mixture consisting essentially of: i) the histamine-containing biological sample in medium and ii) an aqueous solution of the histamine releaser and a pre-selected concentration of the physiologically acceptable excipient, wherein the histamine releaser in the comparative mixture is present in a concentration which is substantially the same as the concentration of histamine releaser in the reference mixture of step a); c) optionally repeating step b) one or more times with a comparative mixture having a different pre-selected concentration of the physiologically acceptable excipient; and d) identifying a concentration of the physiologically acceptable excipient sufficient to reduce histamine release from the histamine-containing biological sample in the comparative mixture by at least about 10 percent compared to histamine release from the histamine-containing biological sample in the reference mixture. The identified concentration of step d) is the concentration of the physiologically acceptable excipient that is sufficient to suppress pharmaceutically-induced histamine release in an animal being treated with a histamine releaser.

3.) In Vivo Methods

Although not the most preferred method, the concentration of the excipient for use in the present invention can be determined by a method comprising the steps of: a) intravenously administering a rapid bolus or rapid infusion of a pharmaceutical formulation comprising a therapeutically effective amount of the histamine releaser and a pre-selected concentration of the excipient; b) optionally repeating step a) one or more times with a pharmaceutical formulation comprising a different pre-selected concentration of the excipient; and c) qualitatively or quantitatively measuring suppression of histamine release in vivo as compared to a pharmaceutical formulation containing substantially no physiologically acceptable excipient, wherein the suitable concentration of excipient is the concentration sufficient to qualitatively or quantitatively suppress histamine release in vivo.

The formulation of step a) can be prepared according to any of the methods of the present invention. Step c) of qualitatively or quantitatively measuring suppression of histamine release can be carried out using the methods described below.

4.) Concentrations of Excipients

The preferred concentrations of excipient(s) varies depending upon factors such as the category of or the particular excipient employed and whether the excipient is a combination of two or more excipients.

In general, when the excipient is a divalent inorganic salt, the concentration of the excipient will be at least about 15 mM, preferably from about 15 mM to about 200 mM, more preferably from about 25 mM to about 75 mM, regardless of whether the excipient is employed singly or in combination with one or more additional excipients. In the embodiment of the invention wherein the excipient is a single divalent inorganic salt, preferred concentrations of the excipient will be from about 25 mM to about 75 mM and more preferably about 50 mM. In the embodiment wherein the excipient is calcium chloride, preferred concentrations of excipient will be from about 15 mM to about 200 mM, more preferably from about 25 mM to about 75 mM, and most preferably about 50 mM.

When the divalent inorganic salt is employed in combination with one or more additional excipients, the concentration of the divalent inorganic salt may be lower than about 15 mM, particularly as low as about 10 mM, and is preferably from about 10 mM to about 75 mM and more preferably from about 25 mM to about 50 mM.

In general, when the excipient is an organic carboxylic acid, the concentration of the excipient will be at least about 15 mM, preferably from about 15 mM to about 300 mM, more preferably from about 25 mM to about 75 mM, regardless of whether the excipient is employed singly or in combination with one or more additional excipients. In the embodiment of the invention wherein the excipient is a single organic carboxylic acid, preferred concentrations of the excipient will be from about 25 mM to about 75 mM and more preferably about 50 mM. In the embodiment wherein the excipient is citric acid, preferred concentrations of excipient will be from about 15 mM to about 200 mM, more preferably from about 25 mM to about 75 mM, and most preferably about 50 mM.

When the organic carboxylic acid is employed in combination with one or more additional excipients, the concentration of the organic carboxylic acid may be lower than about 15 mM, particularly as low as about 10 mM, and is preferably from about 10 mM to about 100 mM, more preferably from about 15 mM to about 75 mM and most preferably from about 25 mM to about 50 mM.

In the embodiment wherein the excipient is phosphoric acid, the concentration of the excipient will typically be from about 6 mM to about 100 mM, regardless of whether the excipient is employed singly or in combination with one or more additional excipients.

In general, when the excipient is an amino acid, the concentration of the amino acid will be at least about 5 mg/mL, preferably from about 10 mg/mL to about 100 mg/mL, more preferably from about 10 mg/mL to about 50 mg/mL, and most preferably from about 10 mg/mL to about 30 mg/mL, regardless of whether the excipient is employed singly or in combination with one or more additional excipients. In the embodiment of the invention wherein the excipient is a single amino acid, preferred concentrations of the excipient will be from about 10 mg/mL to about 50 mg/mL, and more preferably between about 10 mg/mL and about 30 mg/mL, and most preferably about 12.5 mg/mL In particular when the excipient is glycine or lysine, preferred concentrations of the excipient will be from about 10 mg/mL to about 100 mg/mL, more preferably from about 10 mg/mL to about 30 mg/mL, and most preferably about 12.5 mg/mL.

When the amino acid is employed in combination with one or more additional excipients, the concentration of the amino acid may be lower than about 5 mg/mL, particularly as low as about 2 mg/mL, and is preferably from about 5 mg/mL to about 50 mg/mL, more preferably from about 10 mg/mL to about 30 mg/mL and most preferably about 12.5 mg/mL.

The concentration of the amino acids is provided in mg/mL units for convenience, however, one skilled in the art can readily calculate the corresponding concentrations of amino acid in mM units by using the molecular weight of the particular amino acid employed. For example, the molecule weight of glycine is 75, and according a 12.5 mg/mL concentration of glycine corresponds to 166.5 mM.

In the embodiment wherein the excipient is a chelating agent, the concentration of the chelating agent will be at least about 0.02%, preferably from about 0.02% to about 1%, more preferably from about 0.1% to about 0.5%, regardless of whether the excipient is employed singly or in combination with one or more additional excipients. In the embodiment of the invention wherein the excipient is a single chelating agent, preferred concentrations of the excipient will be from about 0.02% to about 1%, more preferably from about 0.1% to about 0.5%, and most preferably about 0.1%. In particular, preferred concentrations of EDTA will be between about 0.02% and about 1%, more preferably from about 0.1% to about 0.5%, and most preferably about 0.1%. Percentages are based upon weight unless otherwise indicated.

When employed in combination with one or more additional excipients, the concentration of the chelating agents are preferably from about 0.05% to about 1% and more preferably about 0.1%.

The concentration of the chelating agents is provided in % units for convenience, however, one skilled in the art can readily calculate the corresponding concentrations of chelating agents in mM units by using the molecular weight of the particular chelating agent employed. For example, the molecule weight of EDTA (free acid) is 292.2, and accordingly a 0.1% concentration of EDTA corresponds to 2.69 mM.

In the embodiment wherein the excipient is albumin, the concentration of the excipient will typically be from about 1 mg/mL, preferably from about 1 mg/mL to about 25 mg/mL, more preferably from about 5 mg/mL to about 15 mg/mL, and most preferably about 10 mg/mL, regardless of whether the excipient is employed singly or in combination with one or more additional excipients.

To further illustrate specific concentrations of the excipient(s) according to the present invention, the following embodiments including two or more excipients are provided. In one embodiment, the excipient is a combination of citric acid in a concentration of not less than about 15 mM, preferably from about 15 mM to about 100 mM and more preferably about 50 mM, and EDTA in a concentration of from about 0.02% to about 1%, preferably from about 0.1% to about 0.5% and more preferably about 0.1%. In one preferred embodiment, the excipient is a combination of citric acid in a concentration of not less than about 15 mM, preferably from about 15 mM to about 100 mM and more preferably about 50 mM, and calcium chloride in a concentration of not less than about 15 mM, preferably from about 25 mM to about 75 mM and more preferably about 50 mM. In one embodiment, the excipient is a combination of citric acid in a concentration of not less than about 15 mM, preferably from about 15 mM to about 100 mM and more preferably about 50 mM, and glycine in a concentration of from about 10 mg/mL to about 100 mg/mL, preferably from about 10 mg/mL to about 30 mg/mL and more preferably about 12.5 mg/mL. In one embodiment the excipient is a combination of citric acid in a concentration of not less than about 15 mM, preferably from about 15 mM to about 100 mM and more preferably about 50 mM, glycine in a concentration of from about 10 mg/mL to about 100 mg/mL, preferably from about 10 mg/mL to about 30 mg/mL and more preferably about 12.5 mg/mL, and EDTA in a concentration of from about 0.02% to about 1%, preferably from about 0.1% to about 0.5% and more preferably about 0.1%. Other specific examples of combinations of excipients will be readily determinable by those skilled in the art based upon the foregoing description for determining appropriate concentrations and these specific examples.

D. Combining the Histamine Releaser and the Excipient

The step of combining a therapeutically effective amount of the histamine releaser with the concentration of excipient may be carried out by any suitable means known to those skilled in the art. For example, the histamine releaser and excipient may be admixed in solid phase. Alternatively, either the histamine releaser or the excipient may be solubilized or suspended in a suitable physiologically acceptable diluent, and the other component may be added thereto and solubilized or suspended in the diluent. In one preferred embodiment, the excipient is solubilized in a physiologically acceptable diluent and the histamine releaser is added to the solution containing the excipient solubilized therein. If desired for optimization of the formulation (as described below), the pH of the solution containing the one component in diluent, i.e., either the excipient or the histamine releaser, may be adjusted prior to the addition of the other component. In one preferred embodiment, the histamine releaser and excipient are combined by solubilizing the excipient in a physiologically acceptable diluent, adjusting pH and then adding the histamine releaser to the diluent and solubilizing therein.

E. Methods for Optimizing the Formulation with pH

Aggregation of the histamine releaser and histamine release in vivo may be affected in some circumstances by pH. The pH of the formulation containing the histamine releaser can also play a role in the charge, ionic state or solvation capabilities of the histamine releaser In some cases, pH can play a beneficial role in the physical and/or chemical stabilization of certain histamine releasers in solution. For example, certain non-steroidal neuromuscular blockers, such as Compound 1, are known to be more chemically stable at acidic pH, preferably a pH of between about 2 and about 5. For these reasons, it may be desirable or advantageous in some cases to evaluate comparative solutions and mixtures of differing pH, for the purpose of optimizing the pharmaceutical formulations according to the present invention, and for maximizing the suppression of pharmaceutically-induced histamine release.

Thus, according to one embodiment of the present invention the pharmaceutical formulation is optimized for pH. The method for optimizing the pharmaceutical formulation for pH comprises the steps of: a) measuring aggregation of the histamine releaser in a reference solution consisting essentially of the histamine releaser in a concentration at or above the critical micelle concentration in an aqueous solution; b) measuring aggregation of the histamine releaser in a comparative solution consisting essentially of the histamine releaser and a pre-selected or pre-determined concentration of the physiologically acceptable excipient in the aqueous solution, wherein the concentration of the histamine releaser in the comparative solution is substantially the same as the concentration of the histamine releaser in the reference solution, and wherein the comparative solution has a pre-selected pH; c) optionally repeating step b) one or more times with a comparative solution having substantially the same or a different pre-selected concentration of physiologically acceptable excipient and a different pre-selected pH, and d) identifying the pH of the comparative solution which provides the optimum reduction in aggregation of the histamine releaser in the comparative solution. The identified pH of step d) is the pH for preparing an optimized pharmaceutical formulation according to the present invention.

According to another embodiment the pharmaceutical formulation prepared according to the methods of the present invention is optimized for pH using the method comprising the steps of: a) measuring histamine release from a histamine-containing biological sample in a reference mixture consisting essentially of: i) the histamine-containing biological sample in a medium and ii) an aqueous solution of the histamine releaser at a concentration sufficient to cause histamine release from the histamine-containing biological sample; b) measuring histamine release from the histamine-containing biological sample in a comparative mixture consisting essentially of: i) the histamine-containing biological sample in medium and ii) an aqueous solution of the histamine releaser and a pre-selected concentration of the physiologically acceptable excipient, wherein the histamine releaser in the comparative mixture is present in a concentration which is substantially the same as the concentration of histamine releaser in the reference mixture of step a) and wherein the comparative mixture has a pre-selected pH; c) optionally repeating step b) one or more times with a comparative mixture having substantially the same or a different pre-selected concentration of physiologically acceptable excipient and a different pre-selected pH, and d) identifying the pH of the comparative mixture which provides the optimum reduction of histamine release from the histamine-containing biological sample in the comparative mixture. The identified pH of step d) is the pH for preparing an optimized pharmaceutical formulation according to the present invention.

Based upon the preceding examples, one skilled in the art can adapt the teachings above to optimize the pharmaceutical formulations of the present invention regardless of the method which is employed for determining the concentration of excipient. The present invention expressly contemplates using such methods to optimize the pH of the pharmaceutical formulations of the present invention.

The optimum pharmaceutical formulation though, will also take into account the effect of the pH of the formulation on the stability of the particular histamine releaser in the formulation. As noted above some histamine releasers are more physically and/or chemically stable at an acidic pH. Other histamine releasers may be more physically and/or chemically stable at a basic pH.

As will be apparent to those skilled in the art, the pharmaceutical formulations prepared according to the methods of the present invention may be adjusted for pH by titrating formulations of histamine releaser and physiologically acceptable excipient(s) with an agent suitable for adjusting pH. Agents suitable for adjusting pH will be apparent to those skilled in the art and can include for example acids, bases, pH buffers and salts.

Typically, the pH of the optimized pharmaceutical formulations of the present invention will be adjusted as necessary to obtain a pH of the pharmaceutical formulation which is between about 2 and about 10. In one preferred embodiment the pH of the optimized pharmaceutical formulation will be between about 2 and about 8. In one preferred embodiment, the pH of the optimized pharmaceutical formulation will be between about 2 and about 5, more preferably between about 2 and about 4. In the embodiment of the present invention wherein the histamine releaser is Compound 1, the optimized pharmaceutical formulation will typically have a pH of from about 2 to about 5, preferably from about 2 to about 4, and more preferably about 3.

IV. Formulations

The pharmaceutical formulations prepared according to any of the foregoing methods of the present invention may include only the therapeutically effective amount of the histamine releaser and the concentration of the physiologically acceptable excipient. However, in preferred embodiments, the pharmaceutical formulations of the invention also include a physiologically acceptable diluent or vehicle. The diluent facilitates the delivery of the histamine releaser and the excipient to the animal being treated therewith. The selection of a suitable diluent will depend upon the type of pharmaceutical formulation (e.g., solution, dispersion, emulsion, etc.), and is readily determined by those skilled in the art of pharmaceutical sciences.

The pharmaceutical formulations of the invention are in a form suitable for parenteral administration, and preferably in a form suitable for intravenous administration. Formulations suitable for intravenous administration include aqueous sterile injection solutions, aqueous and non-aqueous sterile suspensions, and sterile emulsions.

Aqueous sterile injection solutions typically comprise the histamine releaser and excipient in a physiologically acceptable diluent such as water for injection, sodium chloride for injection, or dextrose for injection. The sterile injection solutions may also contain other physiologically acceptable additives such as other acids (e.g., hydrochloric acid) and bases (e.g., sodium hydroxide) for pH adjustment, pH buffers, and co-solvents. Examples of suitable co-solvents which can be employed in the formulations of the present invention include but are not limited to ethanol, propylene glycol, benzyl alcohol and combinations thereof. Other suitable additives will be apparent to those skilled in the art. Sterile injection solutions may be prepared using conventional techniques of pharmaceutical sciences.

Aqueous and non-aqueous sterile suspensions can include, in addition to the histamine releaser, excipient, diluent, and additives previously mentioned, suspending agents and thickening agents, and liposomes or other microparticulate systems. Non-aqueous sterile suspensions, may employ water, parabens, glycerol, soybean oil, safflower oil, and the like, and also combinations thereof as the diluent. Suspensions may be prepared using techniques known the in art of pharmaceutical sciences.

Sterile emulsions can include oil-in-water emulsions and water-in-oil emulsions. Emulsions may include glycerol, soybean oil, safflower oil, and the like and combinations thereof as the oil phase. Sterile emulsions may be prepared using techniques known the in art of pharmaceutical sciences. Emulsions may include the other additives previously mentioned as well.

The formulations may also be presented as lyophilized solids for reconstitution. Such lyophilized formulations are typically reconstituted with water for injection, sodium chloride for injection or dextrose solution. Lyophilized formulations may include conventional lyophilization bulking agents such as β-cyclodextrin and lactose. Such formulations are typically presented in unit dosage forms such as vials or disposable injection devices. They may also be presented in multi-dose forms such as a bottle from which the appropriate dose may be withdrawn. All such formulations should be sterile.

The appropriate dosage of histamine releaser for inclusion in the formulations of the invention will depend upon the particular histamine releaser and the desired therapeutic effect. Advantageously, conventional dosages of these agents can be employed in the methods and formulations of the present invention.

Preferred formulations of the present invention include a neuromuscular blocker, most preferably Compound 1, as the histamine releaser and one or more excipients, in a form suitable for intravenous administration. Preferred excipients for use in the formulations of the present invention may be selected from the group consisting of divalent inorganic salts, organic carboxylic acids, phosphoric acid, amino acids, chelating agents, albumins and combinations thereof. More preferably, the formulation also includes a diluent selected from the group consisting of water for injection, sodium chloride for injection and dextrose solutions. The concentration of neuromuscular blocker is typically from about 1 mM to about 55 mM. The appropriate concentration of excipient is determined according to the preceding methods.

In one preferred embodiment, the formulation comprises a therapeutically effective amount of (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride or a pharmaceutically acceptable salt thereof, together with citric acid in a concentration of from about 25 to about 75 mM, most preferably about 50 mM.

In one embodiment, the formulation comprises a therapeutically effective amount of (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride or a pharmaceutically acceptable salt thereof, together with EDTA in a concentration of from about 0.1% to about 0.5%, most preferably about 0.1%.

In one embodiment, the formulation comprises a therapeutically effective amount of (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride or a pharmaceutically acceptable salt thereof, together with a combination of citric acid in a concentration of from about 25 to about 75 mM, most preferably about 50 mM, and EDTA in a concentration of from about 0.1% to about 0.5%, most preferably about 0.1%.

In one embodiment, the formulation comprises a therapeutically effective amount of (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride or a pharmaceutically acceptable salt thereof, together with calcium chloride in a concentration of from about 25 to about 75 mM, most preferably about 50 mM.

In one embodiment, the formulation comprises a therapeutically effective amount of (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride or a pharmaceutically acceptable salt thereof, together with a combination of citric acid in a concentration from about 25 to about 75 mM, most preferably about 50 mM, and calcium chloride in a concentration from about 25 to about 75 mM, most preferably about 50 mM.

In one embodiment, the formulation comprises a therapeutically effective amount of (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride or a pharmaceutically acceptable salt thereof, together with glycine in a concentration of from about 10 mg/mL to about 30 mg/mL, preferably about 12.5 mg/mL.

In one embodiment, the formulation comprises a therapeutically effective amount of (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride or a pharmaceutically acceptable salt thereof, together with a combination of glycine in a concentration of from about 10 mg/mL to about 30 mg/mL, preferably about 12.5 mg/mL, and EDTA in a concentration of from about 0.1% to about 0.5%, most preferably about 0.1%.

In one embodiment, the formulation comprises a therapeutically effective amount of (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride or a pharmaceutically acceptable salt thereof, together with a combination of glycine in a concentration of from about 10 mg/mL to about 30 mg/mL, preferably about 12.5 mg/mL, and citric acid in a concentration of from about 25 to about 75 mM, most preferably about 50 mM.

In one embodiment, the formulation comprises a therapeutically effective amount of (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride or a pharmaceutically acceptable salt thereof, together with a combination of glycine in a concentration of from about 10 mg/mL to about 30 mg/ml, preferably about 12.5 mg/mL, citric acid in a concentration of from about 25 to about 75 mM, most preferably about 50 mM, and EDTA in a concentration of from about 0.1% to about 0.5%, most preferably about 0.1%. Particularly preferred of the foregoing specific examples of pharmaceutical formulations are formulations having a pH between about 2 and about 5, more preferably between about 2 and about 4 and most preferably about 3. In the formulations noted above, pH adjustment to the ranges noted may or may not be necessary depending upon the particular excipients and concentrations employed.

V. Methods for Suppressing Histamine Release

The present invention also provides methods for suppressing pharmaceutically-induced histamine release in an animal being treated with a histamine releaser. "Pharmaceutically-induced histamine release" as used herein refers to histamine release in vivo which is induced or at least partially caused by the intravenous rapid bolus or rapid infusion administration of a histamine releaser. Pharmaceutically-induced histamine release is described in Goodman & Gilman's The PHARMACOLOGICAL BASIS OF THERAPEUTICS, 9th ed. McGraw-Hill, New York, (1996) pp. 581–593.

As used herein, to "suppress pharmaceutically-induced histamine release" means to substantially completely prevent histamine release or reduce the amount or the rate of histamine release from histamine-containing cells, tissues or fluids in vitro upon exposure to a histamine releaser; or to substantially completely prevent histamine release, or reduce the amount or the rate of histamine release from histamine-containing cells, tissues or fluids in vivo upon administration of a formulation containing a histamine releaser to an animal. More specifically, "suppression of pharmaceutically-induced histamine release" in vivo refers to suppression of histamine release in vivo upon intravenous administration of a histamine releaser as a rapid bolus or rapid infusion. Suppression of pharmaceutically-induced histamine release can be observed qualitatively and/or quantitatively.

Pharmaceutically-induced histamine release can be qualitatively observed by intravenously administering a rapid bolus or rapid infusion of the histamine releaser to the animal and observing the physical manifestations described above, which are associated with elevated plasma and/or tissue concentrations of histamine. Suppression of pharmaceutically-induced histamine release, therefore is qualitatively observed by intravenously administering to the animal being treated, a rapid bolus or rapid infusion of any of the pharmaceutical formulations of the present invention and observing comparatively less severe physiological manifestations, or even an absence of the physiological manifestations, associated with elevated plasma and/or tissue histamine levels.

Suppression of pharmaceutically-induced histamine release can be quantitatively observed by intravenously administering to the animal being treated a rapid bolus or rapid infusion of the pharmaceutical formulation according to the present invention and observing, and measuring the plasma and/or tissue histamine levels present in the animal subsequent to administration. Plasma histamine levels present in the animal subsequent to administration can be measured by withdrawing a blood sample from the animal after administration of the pharmaceutical formulation. The blood sample is preferably withdrawn from the region at or near the site of administration of the pharmaceutical formulation. Tissue histamine levels present in the animal subsequent to administration can be measured by taking a tissue sample from the animal after administration of the pharmaceutical formulation. The sample is preferably taken from the region at or near the site of administration of the pharmaceutical formulation. Histamine levels present in either the plasma or tissue sample can be measured using the techniques described above for detecting histamine release from a biological sample, e.g., ELISA, RIA and fluorometric assays.

In general, the methods for suppressing pharmaceutically-induced histamine release in an animal being treated with a histamine releaser comprise administering to the animal, any pharmaceutical formulation according to the present invention. In preferred methods, the pharmaceutical formulation will include an excipient selected from the group consisting of divalent inorganic salts, organic carboxylic acids, phosphoric acid, amino acids, chelating agents, albumins and combinations thereof.

The step of administering comprises parenterally administering the pharmaceutical formulation to the animal, more preferably, intravenously administering the pharmaceutical formulation, and most preferably intravenously administering the pharmaceutical formulation as a rapid bolus or rapid infusion. The formulations of the present invention advantageously permit intravenous administration as a rapid bolus or rapid infusion, while suppressing the concomitant release of histamine that is typically observed with administration of conventional formulations of histamine releasers by this technique.

More specifically, one method for suppressing pharmaceutically-induced histamine release in an animal being treated with a histamine releaser comprises administering to an animal in need thereof, a pharmaceutical formulation comprising a therapeutically effective amount of the histamine releaser and a concentration of physiologically acceptable excipient which concentration, when combined in an aqueous solution with the histamine releaser at or above the critical micelle concentration, is sufficient to reduce aggregation of the histamine releaser in the aqueous solution by at least about 25 percent compared to aggregation of the histamine releaser in an aqueous solution containing substantially no physiologically acceptable excipient.

Another method for suppressing pharmaceutically-induced histamine release in an animal being treated with a histamine releaser comprises administering to an animal in need thereof, a pharmaceutical formulation comprising a therapeutically effective amount of the histamine releaser and a concentration of physiologically acceptable excipient which concentration, is determined by the method comprising the steps of: a) measuring aggregation of the histamine releaser in a reference solution consisting essentially of the histamine releaser in a concentration at or above the critical micelle concentration in an aqueous solution; b) measuring aggregation of the histamine releaser in a comparative solution consisting essentially of the histamine releaser and a pre-selected concentration of the physiologically acceptable excipient in the aqueous solution, wherein the concentration of the histamine releaser in the comparative solution is substantially the same as the concentration of the histamine releaser in the reference solution; c) optionally repeating step b) one or more times with a comparative solution having a different pre-selected concentration of the physiologically acceptable excipient; d) identifying a concentration of physiologically acceptable excipient that is sufficient to reduce aggregation of the histamine releaser in the comparative solution by at least about 25 percent compared to aggregation of the histamine releaser in the reference solution; wherein the identified concentration of step d) is the concentration of the physiologically acceptable excipient that is sufficient to suppress pharmaceutically-induced histamine release in an animal being treated with a histamine releaser and is the concentration of physiologically acceptable excipient for combining with the histamine releaser to prepare the pharmaceutical formulation for administration to the animal being treated therewith.

Another method for suppressing pharmaceutically-induced histamine release in an animal being treated with a histamine releaser comprises administering to an animal in need thereof, a pharmaceutical formulation comprising a therapeutically effective amount of the histamine releaser and a concentration of physiologically acceptable excipient which concentration, is determined by the method comprising the steps of: a) measuring histamine release from a histamine-containing biological sample in a reference mixture, b) measuring histamine release from the histamine-containing biological sample in a comparative mixture, c) optionally repeating step b) one or more times with a comparative mixture having a different pre-selected concentration of the physiologically acceptable excipient; and d) identifying a concentration of the physiologically acceptable excipient sufficient to reduce histamine release from the histamine-containing biological sample in the comparative mixture by at least about 10 percent compared to histamine release from the histamine-containing biological sample in the reference mixture; wherein the identified concentration of step d) is the concentration of physiologically acceptable excipient for combining with the histamine releaser to prepare the pharmaceutical formulation. The reference mixture consists essentially of: i) the histamine-containing biological sample in a medium and ii) an aqueous solution of the histamine releaser at a concentration sufficient to cause histamine release from the histamine-containing biological sample. The comparative mixture consists essentially of: i) the histamine-containing biological sample in medium and ii) an aqueous solution of the histamine releaser and a pre-selected concentration of the physiologically acceptable excipient, wherein the histamine releaser in the comparative mixture is present in a concentration which is substantially the same as the concentration of histamine releaser in the reference mixture of step a).

Histamine release in vivo may be triggered differently among and even within animal species (e.g., different sites may be involved and different animals may have different sensitivities). Accordingly the methods of treatment may be optimized by one skilled in the art, for a particular species or individual subject. The methods of treatment are useful for the treatment of a variety of animals, preferably mammals, including humans, dogs, and primates (e.g., monkeys) and most preferably humans.

The present invention also comprises methods for preventing cardiovascular and respiratory effects mediated by pharmaceutically-induced histamine release in an animal being treated with a histamine-releaser. "Cardiovascular and respiratory effects mediated by pharmaceutically-induced histamine release" as used herein refers to cardiovascular and respiratory effects induced by elevated plasma and/or tissue histamine levels, i.e., plasma or tissue histamine levels above normal physiological levels. Such histamine-induced cardiovascular and respiratory effects can include, but are not limited to flushing, hypotension, tachycardia, bronchoconstriction, anaphylactoid reactions and anaphylactic shock, and combinations of any two or more of the foregoing.

The terms "prevent" or "prevention" as used herein with reference to a particular condition refers to a decrease in the incidence and/or severity of the condition, as well as avoidance of the condition.

The method for preventing cardiovascular effects mediated by pharmaceutically-induced histamine release in an animal being treated with a histamine-releaser comprises administering to the animal, any pharmaceutical formulation according to the present invention. By suppressing the histamine release typically induced by the intravenous rapid bolus or rapid infusion administration of a histamine releaser, the undesirable cardiovascular effects resulting from elevated plasma and tissue histamine levels are prevented.

VI. Kits

The present invention also includes a kit useful for the preparation of pharmaceutical formulations of histamine releasers according to the present invention. The kit comprises: a) a physiologically acceptable excipient, and b) instructions for preparing the pharmaceutical formulation according to the present invention.

The excipient is preferably selected from the group consisting of divalent inorganic salts, organic carboxylic acids, phosphoric acid, amino acids, chelating agents, albumins and combinations thereof. More preferably, the physiologically acceptable excipient is selected from the group consisting of calcium chloride, sodium sulfate, magnesium sulfate, tartaric acid, maleic acid, acetic acid, citric acid, succinic acid, glucuronic acid, phosphoric acid, glycine, lysine, arginine, EDTA, bovine serum albumin, human serum albumin and combinations thereof.

The instructions include instructions for combining the histamine releaser with the concentration of the excipient in order to prepare any of the pharmaceutical formulations of the present invention. More specifically, the instructions can include instructions for combining the histamine releaser with a concentration of the excipient which is sufficient, when combined in an aqueous solution with the histamine releaser at or above critical micelle concentration, to reduce aggregation of the histamine releaser in the aqueous solution by at least about 25 percent compared to aggregation of the histamine releaser in the aqueous solution containing substantially no physiologically acceptable excipient. The instructions can include instructions for combining the histamine releaser with the excipient in concentrations sufficient to suppress pharmaceutically-induced histamine release from the animal being treated with the histamine releaser.

In a preferred embodiment, the instructions will include the precise amount of histamine releaser required to achieve the desired therapeutic, diagnostic or medicinal effect, which amount will be specific for the particular histamine releaser employed. Thus, the instructions may include specific amounts for several different specific histamine releasers, which specific amount for each specific histamine releaser is a therapeutically effective amount.

In another preferred embodiment, the instructions will include the precise amount of excipient for combining with the histamine releaser, which amount will be specific for the particular excipient or combination of excipients for use with the particular histamine releaser with which the excipient will be combined to prepare the pharmaceutical formulation. The precise amount of excipient provided, will have been pre-determined using any one or more of the methods of the present invention for determining the concentration of excipient for combining with the histamine releaser to prepare the pharmaceutical formulation.

The kit may also include the histamine releaser. In this embodiment, the instructions include instructions for preparing a pharmaceutical formulation according to the present invention by combining a therapeutically effective amount of the provided histamine releaser with a concentration of excipient that is sufficient to suppress pharmaceutically induced histamine release from the animal being treated with the histamine releaser and to whom the prepared formulation will be administered. In one preferred embodiment, the kit includes the histamine releaser, (Z)-2-chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride or a pharmaceutically acceptable salt thereof.

Depending upon the particular histamine releaser and excipients employed in the preparation of the pharmaceutical formulation, the instructions may also include instructions for adjusting pH of the pharmaceutical formulation to from about 2 to about 8, preferably from about 2 to about 5 and more preferably to about 3.

The kit may also include additional components. For example, the kit may also include a physiologically acceptable diluent for solubilizing and/or reconstituting the histamine releaser and the physiologically acceptable excipient. In this embodiment, the instructions include instructions for combining the histamine releaser and the physiologically acceptable excipient in the diluent. As another example, the kit may include one or more containers for combining the histamine releaser and the excipient.

The following examples are intended for illustration only and are not intended to limit the scope of the invention, the invention being defined by the claims.

As used herein: "mM" means millimolar; "nM" means nanomolar; "mg/mL" means milligrams per milliliter; "%" means percent by weight; "NaCl" means sodium chloride; "D2O" means deuterated water; "D2O saline" means deuterated saline solution; "NaOD" means deuterated sodium hydroxide; "DCl" means deuterated hydrochloric acid; "$d_4$-citrate" means deuterated citric acid; "$CaCl_2$" means calcium chloride; "pD" means pH uncorrected for the deuterium isotope effect; "$\mu L$" means microliters; "$\mu m$" means micrometer; "MHz" means megahertz; "ppm" means parts per million; "° C." means degrees Centigrade; "mmHg" means millimeters of mercury; and "Compound 1" means (Z)-2-chloro-1-{3-{(1R,2S)-6,7-dimethoxy-2-methyl-1-[(3,4,5-trimethoxyphenyl)methyl]-1,2,3,4tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride or a pharmaceutically acceptable salt thereof.

EXAMPLE 1

Surface Tension Analysis

The surface tension properties of the histamine liberating agent can be evaluated using the DuNouy ring method. This and other methods for evaluating surface tension properties are described in the literature. See, PHYSICAL PHARMACY: PHYSICAL CHEMICAL PRINCIPLES IN THE PHARMACEUTICAL SCIENCES, Editors: Alfred Martin, James Swarbrick, Arthur Cammarata, Third Edition, Lea & Febiger, Philadelphia, 1983.

The DuNuoy tensiometer, commercially available from Kruss GMBH, Hamburg Germany, is used for measuring the surface and interfacial tension of liquids. The principle of the instrument depends on the fact that the force necessary to detach a platinum-iridium ring immersed at the surface is proportional to the surface tension.

The force required to detach the ring in this manner is provided by a torsion wire and is recorded in dynes on a calibrated dial. The surface tension is given by the formula:

$$\Upsilon = \frac{\text{dial reading in dynes}}{2 \times \text{ring circumference} \times \text{correction factor}}$$

where the ring circumference and the correction factor are equipment specific.

The surface tension of most liquids decreases almost linearly with an increase in temperature, and thus it is necessary to control the temperature of the system when carrying out surface tension determinations.

The tensiometer is calibrated with filtered water and the surface tension of a 50 mg/mL solution of Compound 1 in water is evaluated at room temperature. The solution is diluted to obtain solutions having the following concentrations (mg/mL) of Compound 1: 47.5, 45, 42.5, 40, 37.5, 35, 32.5, 30, 27.5, 25, 22.5, 20, 17.5, 15, 12.5, 10, 5,3,2, and 1.

The surface tension of each solution is evaluated at room temperature and the results are recorded in a curve of surface tension (y-axis) versus concentration of drug (x-axis). The results are reported in FIG. 1. FIG. 1 indicates that Compound 1 is surface active at therapeutically effective doses and reveals concentration dependent surface tension lowering.

Referring to FIG. 1, the change in slope of the surface tension graph with increasing concentration of Compound 1, which occurs at approximately 15–17.5 mg/mL indicates the critical micelle concentration of Compound 1 in water.

EXAMPLE 2

Proton NMR Analysis

A. General Procedures

Compound 1 and excipient (in the various amounts noted below) are dissolved in 200 $\mu L$ of $D_2O$ with 0.15 M NaCl adjusted to pD 3.0 with NaOD and/or DCl for compound stability reasons. Deuterated saline solution is used in the reference solution because critical compound peaks (or signals) overlap when deuterated water is employed. Samples in a titration series are prepared by serial dilutions. All NMR spectra are recorded at 30° C. on a Varian Unity Plus 500 MHz spectrometer. Spectra are referenced to $D_2O$ at 4.65 ppm. All spectra are processed using Varian VNMR® software v6.1a. $T_1$ and $T_2$ relaxation rates are measured using the standard inversion-recovery and Carr-Purcell-Meiboom-Gill (CPMG) experiments respectively, both of which are provided with the Varian software. CPMG experiments are described in M. Bulsing, et al., *J. Chem. Soc. Chem. Commun.* 1201–3 (1981); R. Freeman et al., IN DYNAMIC NMR SPECTROSCOPY, eds. L. Jackman and F. Cotton (1975) pp. 131–162, Academic Press, London and New York; and D. Rabenstein, et al., *J. Magn. Reson.* 64:541–546 (1985).

B. Determination of the Concentration of Compound 1 for the Reference Solution

A series of solutions with increasing concentrations of Compound 1 in $D_2O$ saline, pD 3.0 are prepared and the NMR relaxation rate constants measured. Both $T_1S$ and $T_2S$ are measured because the drug, with a molecular weight of 1064.51, could lie outside the extreme motional narrowing limit for NMR, in which case, $T_1S$ would be expected to decrease and $T_2S$ would be expected to increase with a decrease in aggregation. See, K. Wüthrich, NMR OF PROTEINS AND NUCLEIC ACIDS, (1986) John Wiley & Sons, New York. However, the data show an increase in both $T_1S$ and $T_2S$ with decreasing aggregation, indicating that the drug is still within the extreme motional narrowing limit under these conditions. Table 1 summarizes the $T_1$ and $T_2$ values for the vinyl proton of Compound 1 which is located in the center of the molecule and is observed to exhibit the largest changes.

TABLE 1

| Drug Conc. (mM) | pD | NaCl (mM) | $T_1$ (secs) | $T_2$ (secs) |
|---|---|---|---|---|
| 160 | 3 | 150 | 0.83 | 0.13 |
| 80 | 3 | 150 | 1.20 | 0.38 |
| 40 | 3 | 150 | 2.49 | 1.96 |
| 20 | 3 | 150 | 2.30 | 2.04 |
| 10 | 3 | 150 | 2.05 | — |

The data show that both the $T_1$ and $T_2$ values change as the concentration of drug increases. Although one might be tempted to attribute a portion of the change in $T_1$ and $T_2$ to an expected increase in the viscosity of the solution with increasing concentration of drug (this was observed visually), such a change would be linear in proportion to the change in drug concentration. The data show relatively little change in $T_1$ and $T_2$ values between 10–40 mM of drug, a sharp decrease in $T_1$ and $T_2$ between 40–80 mM of drug, and a smaller decrease in $T_1$ and $T_2$ between 80–160 mM of drug. The sharp decrease of $T_1$ and $T_2$ is evidence that the critical micelle concentration of Compound 1 in $D_2O$ saline is between 40–80 mM. For this reason a concentration of 80 mM was selected as the concentration of the drug for the reference solution.

C. Test Excipient: Citric Acid

A series of solutions containing 80 mM Compound 1 with increasing concentrations of $d_4$-citrate in $D_2O$ saline, pD 3.0, are prepared, and the NMR relaxation rates are measured. The data obtained is summarized in Table 2 and reported graphically in FIG. 2.

TABLE 2

| Drug Conc. (mM) | pD | NaCl (mM) | $D_4$-Citrate (mM) | $T_1$ (secs) | $T_2$ (secs) |
|---|---|---|---|---|---|
| 80 | 3 | 150 | 100 | 1.96 | 0.85 |
| 80 | 3 | 150 | 50 | 2.13 | 1.31 |
| 80 | 3 | 150 | 25 | 2.03 | 0.87 |
| 80 | 3 | 150 | 12.5 | 2.09 | 1.01 |
| 80 | 3 | 150 | 6.25 | 1.24 | 0.69 |
| 80 | 3 | 150 | 3.13 | 1.69 | 0.67 |
| 80 | 3 | 150 | 1.56 | 1.65 | 0.59 |

TABLE 2-continued

| Drug Conc. (mM) | pD | NaCl (mM) | $D_4$-Citrate (mM) | $T_1$ (secs) | $T_2$ (secs) |
|---|---|---|---|---|---|
| 80 | 3 | 150 | 0.78 | 1.53 | 0.57 |
| 80 | 3 | 150 | 0 | 1.20 | 0.38 |

The data show that $T_1$ and $T_2$ values increase with increasing concentration of $d_4$-citrate. This trend is indicative of decreasing aggregation with a maximal effect obtained at 50 mM $d_4$-citrate. Viscosity changes are discounted as having a minimal effect on $T_1$ and $T_2$ values measured, because no visible changes in viscosity are noticed and it is not expected that addition of $d_4$-citrate to an aqueous solution in these concentrations would substantially alter the viscosity.

The data show that a 50 mM concentration of $d_4$-citrate exhibited relaxation rates at least 25 percent slower than the relaxation rate of the reference solution containing the same concentration of the drug (a longer time in secs. for the measured $T_1$ and $T_2$ values is indicative of a slower relaxation rate, which is indicative of reduced or lowered aggregation). Thus, citric acid at a 50 mM concentration is a suitable excipient for decreasing aggregation of Compound 1 in solution.

D. Test Excipient: Citric Acid+Calcium Chloride

A series of solutions containing 80 mM Compound 1 and varying concentrations of $CaCl_2$ and $d_4$-citrate in $D_2O$ saline, pD 3.0, are prepared, and the NMR relaxation rates are measured. The data obtained is summarized in Table 3.

TABLE 3

| Drug Conc. (mM) | pD | NaCl (mM) | D4-Citrate (mM) | $CaCl_2$ (mM) | $T_1$ (secs) |
|---|---|---|---|---|---|
| 80 | 3 | 150 | 0.78 | 100 | 2.78 |
| 80 | 3 | 150 | 50 | 100 | 2.26 |
| 80 | 3 | 150 | 5 | 100 | 2.14 |
| 80 | 3 | 150 | 5 | 50 | 1.94 |
| 80 | 3 | 150 | 5 | 25 | 1.89 |
| 80 | 3 | 150 | 5 | 12.5 | 1.51 |
| 80 | 3 | 150 | 5 | 6.25 | 1.47 |
| 80 | 3 | 150 | 5 | 3.13 | 1.45 |
| 80 | 3 | 150 | 0 | 0 | 1.2 |

As can be seen from the data, all but the two lowest concentrations of $CaCl_2$ produce a change in the $T_1$ value (i.e., a slowing of the relaxation rate) which is greater than 25% as compared to the relaxation rate of the reference solution containing the same concentration of Compound 1. This result indicates that combinations of calcium chloride and citric acid at these concentrations are sufficient to decrease aggregation of Compound 1 by at least about 25%.

The results obtained indicate the excipients at the indicated concentrations which produce a change in the $T_1$ value (i.e., a slowing of the relaxation rate) which is greater than 25% as compared to the relaxation rate of the reference solution containing the same concentration of drug. This result indicates that these excipients and combinations of excipients are sufficient to decrease aggregation of Compound 1 in solution by at least about 25%.

EXAMPLE 3
In Vitro Rat Basophilic Leukemia (RBL) 2H3Cell Studies

Histamine released by Compound 1, in the absence and presence of added excipients using Rat Basophil Leukemia (RBL) 2H3 cells is evaluated. RBL 2H3 is a rat mast cell line which stores preformed histamine. RBL 2H3 cells ($8 \times 10^4$ cells) are seeded on a 96-well plate overnight and treated with of a formulation containing 160 mM of Compound 1 and various concentrations of citric acid (0, 5, 10, 25 and 50 mM) in distilled water at pH 3, for 30 minutes at 37° C. before collecting the cell-free media. The control, using the same cell cultures on the same day, involves exposing the cells to a formulation containing 160 mM of drug and 0 mM of citric acid in distilled water at pH 3. Histamine is quantified using the histamine assay (ELISA) kit commercially available from Immunotech.

Figure 2:
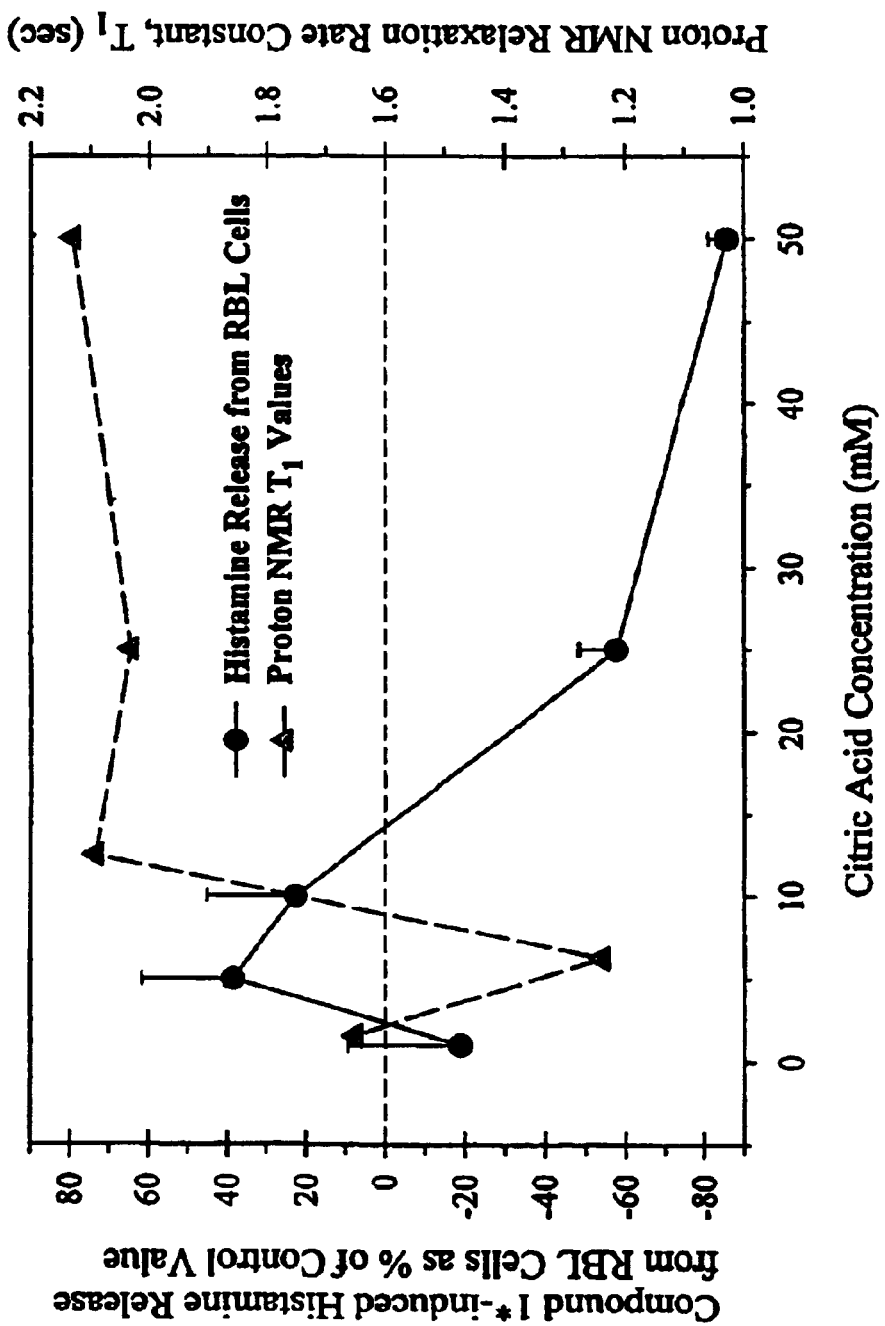
FIG. 2 is a graph depicting (-▲-) the proton NMR relaxation rate ($T_1$ value in secs.) for solutions containing 80 mM (Z)-2-Chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}-4-{3-[(1S,2R)-6,7-dimethoxy-2-methyl-1-(3,4,5-trimethoxyphenyl)-1,2,3,4-tetrahydro-2-isoquinolinio]propyl}-2-butenedioate dichloride (designated "Compound 1"), and various concentrations of $d_4$-citrate (3.13, 6.25, 12.5, 25 and 50 mM) in deuterated saline solution at pD 3, and (-●-) the pharmaceutically-induced histamine release from rat basophilic leukemia cells as a percent of control value, which is induced by exposure of the RBL cells to a formulation containing 160 mM of the same compound, and various concentrations of citric acid (5, 10, 25 and 50 mM) in distilled water at pH 3.

The data obtained is reported graphically in FIG. 2.

FIG. 2 shows the effects, in terms of percent of pharmaceutically-induced histamine release, caused by the drug, versus control, of the various concentrations of citric acid on the inhibition of histamine release from RBL cells in vitro. FIG. 2 shows an inverse relationship between increasing concentrations of citric acid and the percent histamine released from the RBL cells.

FIG. 2 also shows an inverse relationship between histamine release observed in RBL cells with increasing concentration of citric acid and Compound 1 aggregation, as indicated by the NMR relaxation rate ($T_1$), in solutions which contain corresponding concentrations of citric acid.

EXAMPLE 4
Human Blood Studies

Histamine release induced by Compound 1 is quantified in the absence and presence of various excipients in peripheral (venous) blood obtained from human donors. The blood is heparinized upon collection and diluted 1:1 with saline buffer. Excipient solutions are prepared as aqueous solutions at pH 3 and pH 7 by solubilizing the appropriate amount of the specific excipient in water to prepare a solution with the desired concentration of excipient. A sufficient amount of Compound 1 is then added to each excipient solution to obtain a formulation containing 40 mM of drug and the specified concentration of excipient. Formulations are tested at both pH 3 and pH 7 to evaluate the effects of the drug in blood once the formulation is buffered by the blood.

Diluted blood is incubated with the prepared formulations for 5 minutes at 37° C. before collecting cell-free medium. A control is run on the same day, using a formulation containing the same concentration of the drug and no additional excipients. The amount of histamine in the medium is measured utilizing an immunoassay (ELISA) kit commercially available from Immunotech. The results obtained for each formulation are reported in Table 5 below in terms of the percent inhibition of histamine release at the indicated pH based on the control.

TABLE 5

| Excipient Solution Conc. | % Inhibition of Histamine Release | |
|---|---|---|
| | pH 3 | pH 7 |
| glycine 12.5 mg/mL | 75.2 ± 2.1 | 30.4 ± 2.5 |
| EDTA-Na$_2$ 0.1% | 14.1 ± 8.3 | 10.4 ± 5.6 |
| glycine 12.5 mg/mL + EDTA-Na$_2$ 0.1% | 45.4 ± 1.3 | 48.4 ± 1.7 |
| glycine 12.5 mg/mL + citric acid 50 mM | 44.3 ± 4.0 | 40.7 ± 0.7 |
| citric acid 50 mM + EDTA-Na$_2$ 0.1% | 37.9 ± 5.7 | 37.4 ± 1.6 |
| citric acid 50 mM | 90.8 ± 14.6 | 3.5 ± 0.9 |
| succinic acid 50 mM | 77.5 ± 15.4 | 7.2 ± 14.6 |
| glucuronic acid 50 mM | 66.9 ± 9.5 | 16.8 ± 8.5 |
| L-tartaric acid 50 mM | 65.1 ± 13.1 | 0 |
| phosphoric acid 50 mM | 60.4 ± 13.2 | 2.1 ± 8.8 |
| acetic acid 50 mM | 59.9 ± 17.5 | 3.5 ± 0.6 |
| maleic acid 50 mM | 56.3 ± 7.9 | 0 |
| bovine serum albumin 10 mg/mL | 39.8 ± 5.5 | not tested |
| lysine 12.5 mg/mL | 25.8 ± 5.9 | 0 |
| D-aspartic acid 0.32 mg/mL | 13.6 ± 7.7 | 0 |
| arginine 12.5 mg/mL | 0 | 30.4 ± 1.8 |
| magnesium sulphate 50 mM | 0 | 9.5 ± 2.6 |

Values are expressed as means ± SE of duplicate experiments.
* Inhibition expressed as a percent of the histamine released by Compound 1 control in the same assay.

The results reported in Table 5 indicate that several formulations suppress histamine release in human blood. The results demonstrate that this method is useful for screening different excipients at different concentrations and under different pH conditions to determine the appropriate excipients, concentrations and pH for a given drug.

EXAMPLE 5

Formulations

Formulations containing a variety of drugs known or suspected to possess an adverse side-effect potential for histamine release in vivo when administered as a rapid intravenous bolus or infusion are prepared according to the following procedure. The desired amount of excipient is solubilized in filtered water for injection or sodium chloride for injection, pH is adjusted as necessary to obtain a solution having the indicated pH value, the solution is brought to volume with water or sodium chloride for injection to obtain the desired excipient concentration, mixed well. The desired amount of Compound 1 is added, the formulation mixed, and then sterile filtered using 0.22–0.45 μm pore size membrane. The formulations are reported in Table 6.

TABLE 6

| | Drug (conc.) | pH | Excipients |
|---|---|---|---|
| A | Compound 1 (10 mg/mL) | 3 | glycine (12.5 mg/mL) |
| B | Compound 1 (5 or 10 mg/mL) | 3 | EDTA (0.1%) |
| C | Compound 1 (10 mg/mL) | 3 | glycine (12.5 mg/mL) + EDTA (0.1%) |
| D | Compound 1 (10 mg/mL) | 3 | glycine (12.5 mg/mL) + citric acid (50 mM) |

TABLE 6-continued

|    | Drug (conc.) | pH | Excipients |
|----|---|---|---|
| E  | Compound 1 (2 or 10 mg/mL) | 3 | citric acid (50 mM) + EDTA (0.1%) |
| F  | Compound 1 (10 mg/mL) | 3 | citric acid (50 mM) |
| G  | Compound 1 (10 mg/mL) | 3 | $CaCl_2$ (50 mM) |
| H  | Compound 1 (10 mg/mL) | 3 | glycine (12.5 mg/mL) + citric acid (50 mM) + EDTA (0.1%) |
| I  | Compound 1 (10 mg/mL) | 3 | glycine (12.5 mg/mL) + citric acid (50 mM) + $CaCl_2$ (50 mM) |
| J  | morphine sulphate (8, 10 or 15 mg/mL) | 2.5–3.5 | EDTA (0.1–0.2%) |
| K  | morphine sulphate (8, 10 or 15 mg/mL) | 2.5–3.5 | citric acid (60 mM) |
| L  | morphine sulphate (8, 10 or 15 mg/mL) | 2.5–3.5 | glycine (20 mg/mL) |
| M  | morphine sulphate (8, 10 or 15 mg/mL) | 2.5–3.5 | $CaCl_2$ (40 mM) |
| N  | morphine sulphate (8, 10 or 15 mg/mL) | 2.5–3.5 | glycine (15 mg/mL) + EDTA (0.15%) |
| O  | morphine sulphate (8, 10 or 15 mg/mL) | 2.5–3.5 | citric acid (40 mM) + EDTA (0.15%) |
| P  | nalbuphrine HCl (10 or 20 mg/mL) | 3.5–3.7 | EDTA (0.1–0.2%) |
| Q  | nalbuphrine HCl (10 or 20 mg/mL) | 3.5–3.7 | citric acid (60 mM) |
| R  | nalbuphrine HCl (10 or 20 mg/mL) | 3.5–3.7 | glycine (20 mg/mL) |
| S  | nalbuphrine HCl (10 or 20 mg/mL) | 3.5–3.7 | glycine (5 mg/mL) + citric acid (20 mM) + EDTA (0.1%) |
| T  | oxymorphone HCl (1 or 1.5 mg/mL) | 3–5 | citric acid (40 mM) + EDTA (0.2%) |
| U  | oxymorphone HCl (1 or 1.5 mg/mL) | 3–5 | citric acid (60 mM) |
| V  | remifentanil (10 mg/mL) | 3 | glycine (15 mg/mL) |
| W  | remifentanil (10 mg/mL) | 3 | glycine (7 mg/mL) + citric acid (50 mM) + $CaCl_2$ (50 mM) |
| X  | mivacurium Cl (2 mg/mL) | 3.5–5 | glycine (12.5 mg/mL) |
| Y  | mivacurium Cl (2 mg/mL) | 3.5–5 | EDTA (0.1%) |
| Z  | mivacurium Cl (2 mg/mL) | 3.5–5 | glycine (12.5 mg/mL) + EDTA (0.1%) |
| AA | mivacurium Cl (2 mg/mL) | 3.5–5 | glycine (12.5 mg/mL) + citric acid (50 mM) |
| BB | mivacurium Cl (2 mg/mL) | 3.5–5 | citric acid (50 mM) + EDTA (0.1%) |
| CC | mivacurium Cl (2 mg/mL) | 3.5–5 | citric acid (50 mM) |
| DD | mivacurium Cl (2 mg/mL) | 3.5–5 | $CaCl_2$ (50 mM) |
| EE | mivacurium Cl (2 mg/mL) | 3.5–5 | glycine (12.5 mg/mL) + citric acid (50 mM) + EDTA (0.1%) |
| FF | mivacurium Cl (2 mg/mL) | 3.5–5 | glycine (12.5 mg/mL) + citric acid (50 mM) + $CaCl_2$ (50 mM) |
| GG | atracurium besylate (10 mg/mL) | 3.25–3.65 | EDTA (0.1%) |
| HH | atracurium besylate (10 mg/mL) | 3.25–3.65 | glycine (12.5 mg/mL) + EDTA (0.1%) |
| II | atracurium besylate (10 mg/mL) | 3.25–3.65 | citric acid (55 mM) |
| JJ | atracurium besylate (10 mg/mL) | 3.25–3.65 | glycine (12.5 mg/mL) + citric acid (50 mM) + EDTA (0.1%) |
| KK | rocuronium Br (2 or 10 mg/mL) | 4 | EDTA (0.15%) |
| LL | rocuronium Br (2 or 10 mg/mL) | 4 | citric acid (60 mM) |
| MM | rocuronium Br (2 or 10 mg/mL) | 4 | citric acid (60 mM) + EDTA (0.15%) |
| NN | rapacuronium Br (10 mg/mL) | 3–5 | citric acid (60 mM) |

EXAMPLE 6

In Vivo Dog Screen

Using anesthetized beagle dogs, the formulations A–I according to Example 5, are screened for their ability to inhibit pharmaceutically-induced histamine release in vivo. All studies are conducted in accordance with the USDA Animal Welfare Act and with strict adherence to the guidelines set forth by the Institutional Animal Care and Use Committee.

Adult male beagle dogs are anesthetized, intubated and artificially respired. The trachea is intubated under topical anesthesia (2% lidocaine) and ventilation is controlled to end-tidal $CO_2$ concentrations of 25–30 mmHg. The animal is ventilated with a mixture of oxygen and isoflurane to maintain a surgical level of anesthesia throughout the experiment. Rectal temperature, end-tidal $CO_2$, and peripheral $O_2$ saturation (pulse oximetry) were monitored continuously. A catheter is introduced into a femoral artery and connected externally to a pressure transducer. Blood pressure and heart rate are continuously monitored on a chart recorder.

In this experiment, histamine release is evaluated by changes in blood pressure (surrogate cardiovascular marker of histamine release) as well as by measuring the concentrations of plasma histamine. The blood pressure response to histamine release consists of a characteristic brief fall at a latency of about 15–20 seconds from the time of bolus injection. A concomitant tachycardic response is sometimes, but not always, evident.

Blood samples are collected in chilled vials coated with EDTA 1 min before injection and at the peak of the blood pressure response. The plasma is extracted following standard procedures and stored immediately at −70° C. until analyzed. The plasma levels of histamine are determined by immunoassay (ELISA) using a commercially available assay kit from Immunotech.

Each animal serves as its own control: baseline (control) responses to incremental intravenous doses of drug (in sodium chloride for injection, pH 3) are first obtained in each animal. At intervals of 2–3 weeks, an identical dosing protocol is repeated in each animal with a formulation of the drug. The active is administered intravenously in incremental bolus doses at intervals of about 20 minutes. Controls are intermittently re-tested to guard against any drifts in the baseline responses. The results of representative examples are reported in Tables 7A–B below.

TABLE 7-A

Effects of Various Formulations in an Anesthetized Beagle Dog ("Ethan")

| | | Plasma Histamine† Dose of Compound 1 (mg/kg): | | | | Mean Arterial Blood Pressure◆ Dose of Compound 1 (mg/kg): | | | |
|---|---|---|---|---|---|---|---|---|---|
| Week | Formulation | 0.2 | 0.4 | 0.8 | 1.6 | 0.2 | 0.4 | 0.8 | 1.6 |
| 1 | Control | 6 | 90 | 846 | | 1 | 9 | −34 | |
| 3 | A* | 5 | 58 | 454 | 1042 | 1 | −4 | −13 | −38 |
| 5 | G* | 21 | 113 | 585 | 975 | 5 | −5 | −7 | −25 |
| 7 | Control | 48 | 417 | 1125 | | −2 | −2 | −26 | |
| 9 | D* | 4 | 65 | 180 | 707 | 2 | 0 | −13 | −21 |
| 11 | Control | 56 | 269 | 1169 | | 14 | 12 | −31 | |
| 13 | E* | 10 | 104 | 365 | 399 | 12 | −5 | −20 | −29 |
| 15 | A* | 32 | 39 | 1125 | | 1 | 2 | −30 | |
| 17 | Control | 33 | 385 | 1289 | | 2 | −7 | −20 | |

†Increase in plasma histamine (nM) from Baseline
◆Change in Mean Arterial Blood Pressure (mmHg) From Baseline
*Formulation from Example 5

TABLE 7-B

Effects of Various Formulations in an Anesthetized Beagle Dog ("Dexter")

| | | Plasma Histamine† Dose of Compound 1 (mg/kg): | | | Mean Arterial Blood Pressure◆ Dose of Compound 1 (mg/kg): | | |
|---|---|---|---|---|---|---|---|
| Week | Formulation | 0.2 | 0.4 | 0.8 | 0.2 | 0.4 | 0.8 |
| 1 | Control | 29 | 283 | 1191 | 22 | −7 | −34 |
| 3 | A* | 4.4 | 60 | 585 | 13 | 11 | −15 |
| 5 | C* | 6 | 36 | 190 | 3 | 13 | −25 |
| 7 | Control | 9 | 229 | 1269 | 1 | −8 | −33 |
| 9 | B* | 1 | 25 | 181 | 3 | 4 | −15 |
| 11 | Control | 7 | 69 | 531 | −3 | 0 | −51 |
| 13 | D* | 2 | 25 | 367 | 0 | 4 | −47 |
| 15 | B* | 1 | 14 | 394 | 0 | −5 | −32 |
| 17 | Control | 8 | 31 | 1243 | 4 | 9 | −33 |

†Increase in plasma histamine (nM) from Baseline
◆Change in Mean Arterial Blood Pressure (mmHg) From Baseline
*Formulation from Example 5

Tables 7A–B show the effects of several formulations in the anesthetized beagle dog screen. While, in some cases, the magnitude of the histamine-related depressor response to the drug does not appear to be consistently affected by certain formulations, the plasma levels of histamine in each case is reduced, especially at the higher doses. This apparent discrepancy may be attributable to: 1) the selection of these animals is based on their ability to elicit a strong histamine-related response to the drug; and 2) repeated testing at short intervals may have depleted the stores of histamine in these animals, leading to increased histamine receptor sensitivity. Tables 7A–B also display, in some cases, drifts in the control responses to rises in plasma histamine levels and/or falls in mean arterial blood pressure (e.g., Dexter, week 11). These drifts may be attributable to changes in the physical condition of the animal (e.g. bite wounds from other dogs, loss of appetite and weight, etc.) leading to altered stores of histamine and/or altered histamine receptor sensitivity. These examples demonstrate the need for repeating experiments in animals which display more consistent control responses. Also, longer rest periods between testing (3–4 weeks) would help replenish the lost histamine stores and retain histamine receptor sensitivity. The latter regimen of testing was, therefore, successfully applied to the in vivo monkey studies described below.

EXAMPLE 7

In Vivo Monkey Studies

Formulation A, B and E are evaluated (both for NMB and cardiovascular profiles) in anesthetized Rhesus monkeys. These studies are conducted to ensure that the formulation improved the pharmaceutically-induced histamine release profile of Compound 1 without adversely affecting the primary neuromuscular blocking (i.e., therapeutic) properties of the drug in a primate model. All studies are conducted in accordance with the USDA Animal Welfare Act and with strict adherence to the guidelines set forth by the Institutional Animal Care and Use Committee.

The neuromuscular blocking (NMB) properties and the histamine-related cardiovascular effects of the drug formulated in Formulations A, B, and E according to Example 5, is evaluated in anesthetized Rhesus monkeys as follows: Formulation A, 1 monkey; Formulation B, 3 monkeys and Formulation E, 6 monkeys. Transient falls in mean arterial blood pressure (MAP) are monitored as an index of histamine release. Twitch responses of the extensor digitorum of the foot evoked by electrical stimulation of the peroneal nerve are used as an index of neuromuscular activity. NMB parameters measured or computed included: $ED_{95}$ (dose producing 95% suppression of twitch) as an index of potency; onset (time from injection to peak suppression of twitch) and duration of block (time from injection to 95% recovery of twitch).

The formulation of the drug is administered intravenously in incremental bolus doses (0.02–3.2 mg/kg) at intervals of about 30 minutes. The first few doses (0.02–0.08 mg/kg) are administered to obtain data for constructing $ED_{95}$ log-probit curves. The next dose administered is 0.8 mg/kg, after which the dose is successively doubled until a robust MAP response is elicited. Each animal served as its own control.

Control (baseline) NMB and MAP responses are first obtained in each animal. The control formulation includes 10 mg/mL of the drug and 10 mM citric acid in saline at pH 3. At intervals (resting periods) of 3–4 weeks, the effects of the drug in each formulation are re-evaluated in each animal following an identical dosing regimen. The 3–4 week rest period allows the animals to replenish their histamine stores and to recover from the minor surgery of the experiment. In addition, in the three monkeys used in formulation B studies, control experiments are repeated at an interval of 13 weeks (during which period other formulations are evaluated at 3–4 week intervals) to determine the extent of drift in baseline (controls) NMB and MAP responses.

The results of the study are reported in Table 8.

TABLE 8

| Time Sample | Treatment/Dose* of Compound 1 (mg/kg) | Changes in Mean Arterial Blood Pressure (mmHg) |
|---|---|---|
| Formulation B Study Results (n = 3) | | |
| Week 1 Control | 0.05 | 0 ± 1.0 |
| | 0.86 | −12 ± 4.7 |
| | 1.71 | −22 ± 6.0 |
| Week 5 Formulation B | 0.05 | 4 ± 2.9 |
| | 0.77 | 2 ± 1.9 |
| | 1.54 | −11 ± 8.0 |
| | 3.09 | −11 ± 10.2 |
| Week 13 Control | 0.04 | 1 ± 1.9 |
| | 0.86 | −5 ± 3.6 |
| | 1.71 | −21 ± 5.0 |
| Formulation E Study Results (n = 6) | | |
| Week 1 Control | 0.05 | 0 ± 0.5 |
| | 0.81 | −7 ± 3.1 |
| | 1.63 | 15 ± 4.0 |
| Week 5 Formulation E | 0.05 | 3 ± 1.7 |
| | 0.77 | −3 ± 1.6 |
| | 1.54 | −9 ± 3.8 |
| | 3.09 | −16 ± 3.2 |

*Doses of drug in controls and formulation B and E experiments are not identical due to small corrections made based on small differences (~10%) in the content of drug between the 2 drug batches used in these studies. The slight differences in dose do not materially affect the study results.

Table 8 indicates the changes in MAP elicited by formulations B and E versus the controls. Also provided in the table are the effects of the controls re-tested at the end of the formulation B study to determine the fidelity of each response. As shown in the table, both formulations B and E increased the mean dose of drug required to elicit a comparable histamine-related depressor response by a factor of approximately 2 (range: 1- to 4-fold). The large standard errors in these MAP values for formulation B are a function of the limited number of study animals and the variability in the incidence and the magnitude of the responses observed at a given dose. Re-testing of controls at the end of the formulation B study revealed some degree of variability in responses at low doses, however, at higher doses, the responses remained reproducible. The duration of action of Compound 1 appeared to be somewhat shortened by formulation E. None of the NMB properties of the drug appeared to be adversely affected by either formulation. The data indicate that formulation B and E suppressed the pharmaceutically-induced histamine release in the animals being treated with the drug, without adversely affecting the NMB properties of the drug.

Formulation A (n=1) did not appear show a statistically significant change in the effects of the drug on mean arterial blood pressure in the single animal to which it was administered. However, the results obtained are of limited reliability due to the study population of 1.

An additional study is done in three monkeys to enable a direct comparison of the neuromuscular blocking potency of the drug in control formulations versus the drug in formulation E. In this crossover study, several data points (yielding <99.9% block of the extensor digitorum twitch) are obtained with low doses (0.02–0.08 mg/kg) of the controls. After a rest interval of 1 hour, during which nerve stimulation is halted, an identical dosing protocol is followed with the drug in formulation E. The results from this study revealed virtually identical mean $ED_{95}$ values between the controls and formulation E (0.11±0.02 mg/kg) indicating that the formulation did not adversely affect the neuromuscular blocking potency of the drug.

That which is claimed is:

1. A method for preparing a pharmaceutical formulation containing a histamine releaser and a physiologically acceptable excipient, said method comprising combining a therapeutically effective amount of said histamine releaser with a concentration of the physiologically acceptable excipient; wherein said concentration of the physiologically acceptable excipient, when combined in an aqueous solution with the histamine releaser at or above critical micelle concentration, is sufficient to reduce aggregation of the histamine releaser in the aqueous solution by at least about 25 percent compared to aggregation of the histamine releaser in the aqueous solution containing substantially no physiologically acceptable excipient; wherein the histamine releaser is (Z)-2-chloror-1-{(3-{(1R, 2S)-6,7-dimethoxy-2-methyl-1-[(3,4,5-trimethoxyphenyl)methyl]-1,2,3,4 -tetrahydro-2-isoquinolinio}propyl}-4-{3-[(1S, 2R)-6,7-dimethoxy-2-methyl-1-(3,4,5-trimethoxyphenyl)-1,2,3,4 -tetrahydro-2-isoquinolinio]propyl}-2-butenedioate dichloride or a pharmaceutically acceptable salt thereof, and the physiologically acceptable excipient is selected from the group consisting of divalent inorganic salts, organic carboxylic acids, phosphoric acid, amino acids, chelating agents, albumins and combinations thereof.

2. The method according to claim 1, wherein the histamine releaser is a neuromuscular blocker.

3. The method according to claim 1, wherein the physiologically acceptable excipient is selected from the group consisting of calcium chloride, sodium sulfate, magnesium sulfate, tartaric acid, maleic acid, acetic acid, citric acid, succinic acid, glucuronic acid, phosphoric acid, glycine, lysine, arginine, EDTA, bovine serum albumin, human serum albumin and combinations thereof.

4. The method according to claim 1, wherein the concentration of the physiologically acceptable excipient is determined by the steps of:
   a) measuring aggregation of said histamine releaser in a reference solution consisting essentially of said histamine releaser in a concentration at or above the critical micelle concentration in the aqueous solution;
   b) measuring aggregation of said histamine releaser in a comparative solution consisting essentially of said histamine releaser and a pre-selected concentration of the physiologically acceptable excipient in the aqueous solution, wherein the concentration of said histamine releaser in the comparative solution is substantially the same as the concentration of said histamine releaser in the reference solution;

c) optionally repeating step b) one or more times with a comparative solution having a different pre-selected concentration of the physiologically acceptable excipient;

d) identifying a concentration of physiologically acceptable excipient that is sufficient to reduce aggregation of said histamine releaser in the comparative solution by at least about 25 percent compared to aggregation of said histamine releaser in the reference solution;

wherein said identified concentration of step d) is the concentration of the physiologically acceptable excipient for combining with said histamine releaser to prepare the pharmaceutical formulation.

5. A pharmaceutical formulation prepared according to claim 1.

6. The pharmaceutical formulation according to claim 5, wherein said histamine releaser is a neuromuscular blocker.

7. The pharmaceutical formulation according to claim 5, wherein the physiologically acceptable excipient is selected from the group consisting of calcium chloride, sodium sulfate, magnesium sulfate, tartaric acid, maleic acid, acetic acid, citric acid, succinic acid, glucuronic acid, phosphoric acid, glycine, lysine, arginine, EDTA, bovine serum albumin, human serum albumin and combinations thereof.

8. The pharmaceutical formulation according to claim 5, wherein the physiologically acceptable excipient is a combination of any two or more excipients selected from the group consisting of glycine, EDTA, citric acid and calcium chloride.

9. The pharmaceutical formulation according to claim 5, wherein the physiologically acceptable excipient is citric acid in a concentration of from about 15 mM to about 300 mM.

10. The pharmaceutical formulation according to claim 5, wherein the physiologically acceptable excipient is EDTA in a concentration of from about 0.02 percent to about 1 percent.

11. The pharmaceutical formulation according to claim 5, wherein the physiologically acceptable excipient is calcium chloride in a concentration of from about 15 mM to about 200 mM.

12. The pharmaceutical formulation according to claim 5, wherein the physiologically acceptable excipient is a combination of citric acid in a concentration of from about 15 mM to about 100 mM and EDTA in a concentration of from about 0.02 percent to about 1 percent.

13. The pharmaceutical formulation according to claim 5, wherein the physiologically acceptable excipient is a combination of citric acid in a concentration of from about 15 mM to about 100 mM and calcium chloride in a concentration of from about 25 mM to about 75 mM.

14. The pharmaceutical formulation according to claim 5, wherein the physiologically acceptable excipient is glycine in a concentration of from about 10 mg/mL to about 100 mg/mL.

15. The pharmaceutical formulation according to claim 5, wherein the physiologically acceptable excipient is a combination of glycine in a concentration of from about 10 mg/mL to about 100 mg/mL and EDTA in a concentration of from about 0.02 percent to about 1 percent.

16. The pharmaceutical formulation according to claim 5, wherein the physiologically acceptable excipient is a combination of glycine in a concentration of from about 10 mg/mL to about 100 mg/mL and citric acid in a concentration of from about 15mM to about 100 mM.

17. The pharmaceutical formulation according to claim 5, wherein the physiologically acceptable excipient is a combination of glycine in a concentration of from about 10 mg/mL to about 100 mg/mL, citric acid in a concentration of from about 15 mM to about 100 mM, and EDTA in a concentration of from about 0.02 percent to about 1 percent.

18. The pharmaceutical formulation according to claim 5, wherein the physiologically acceptable excipient is citric acid in a concentration of about 50 mM.

19. The pharmaceutical formulation according to claim 5, wherein the physiologically acceptable excipient is EDTA in a concentration of about 0.1 percent.

20. The pharmaceutical formulation according to claim 5, wherein the physiologically acceptable excipient is calcium chloride in a concentration of about 50 mM.

21. The pharmaceutical formulation according to claim 5, wherein the physiologically acceptable excipient is a combination of citric acid in a concentration of about 50 mM and EDTA in a concentration of about 0.1 percent.

22. The pharmaceutical formulation according to claim 5, wherein the physiologically acceptable excipient is a combination of citric acid in a concentration of about 50 mM and calcium chloride in a concentration of about 50 mM.

23. The pharmaceutical formulation according to claim 5, wherein the physiologically acceptable excipient is glycine in a concentration of about 12.5 mg/mL.

24. The pharmaceutical formulation according to claim 5, wherein the physiologically acceptable excipient is a combination of glycine in a concentration of about 12.5 mg/mL and EDTA in a concentration of about 0.1 percent.

25. The pharmaceutical formulation according to claim 5, wherein the physiologically acceptable excipient is a combination of glycine in a concentration of about 12.5 mg/mL and citric acid in a concentration of about 50 mM.

26. The pharmaceutical formulation according to claim 5, wherein the physiologically acceptable excipient is a combination of glycine in a concentration of about 12.5 mg/mL citric acid in a concentration of about 50 mM, and EDTA in a concentration of about 0.1 percent.

27. The pharmaceutical formulation according to claim 5, further comprising a physiologically acceptable diluent.

28. The pharmaceutical formulation according to claim 5, wherein said formulation has a pH of from about 2 to about 8.

29. A method of suppressing pharmaceutically-induced histamine release in an animal being treated with the histamine releaser, said method comprising administering to said animal the pharmaceutical formulation according to claim 5.

30. The method according to claim 29, wherein said step of administering the pharmaceutical formulation comprises intravenously administering the pharmaceutical formulation.

31. A method for preventing cardiovascular and respiratory effects mediated by pharmaceutically-induced histamine release in an animal being treated with the histamine releaser, said method comprising administering to said animal the pharmaceutical formulation according to claim 5.

32. The method according to claim 31, wherein said cardiovascular and respiratory effects mediated by pharmaceutically-induced histamine release are selected from the group consisting of flushing, hypotension, tachycardia, bronchoconstriction, anaphylactoid reactions and anaphylactic shock, and combinations of any two or more thereof.

* * * * *